US006852296B2

(12) United States Patent
Bond et al.

(10) Patent No.: US 6,852,296 B2
(45) Date of Patent: Feb. 8, 2005

(54) PRODUCTION OF ULTRAPURE BISMUTH-213 FOR USE IN THERAPEUTIC NUCLEAR MEDICINE

(75) Inventors: Andrew H. Bond, Arlington Heights, IL (US); E. Philip Horwitz, Naperville, IL (US)

(73) Assignee: PG Research Foundation, Darien, IL (US)

( * ) Notice: Subject to any disclaimer, the term of this patent is extended or adjusted under 35 U.S.C. 154(b) by 385 days.

(21) Appl. No.: 10/159,003

(22) Filed: May 31, 2002

(65) Prior Publication Data

US 2003/0012715 A1 Jan. 16, 2003

Related U.S. Application Data

(60) Provisional application No. 60/372,327, filed on Apr. 12, 2002, and provisional application No. 60/300,141, filed on Jun. 22, 2001.

(51) Int. Cl.[7] .......................... C01G 29/00; C22B 30/00

(52) U.S. Cl. ....................... 423/2; 423/DIG. 7; 210/682

(58) Field of Search .............................. 423/2, DIG. 7, 423/6, 7, 249; 210/682, 635

(56) References Cited

U.S. PATENT DOCUMENTS

| | | |
|---|---|---|
| 4,548,790 A | 10/1985 | Horwitz et al. |
| 4,574,072 A | 3/1986 | Horwitz et al. |
| 4,835,107 A | 5/1989 | Horwitz et al. |
| 5,246,691 A | 9/1993 | Geerlings et al. |
| 5,281,631 A | 1/1994 | Horwitz et al. |
| 5,449,462 A | 9/1995 | Horwitz et al. |
| 5,539,003 A | 7/1996 | Horwitz et al. |
| 5,618,851 A | 4/1997 | Trochimcznk et al. |
| 5,641,471 A | 6/1997 | Geerlings |
| 5,651,883 A | 7/1997 | Horwitz et al. |
| 5,749,042 A | 5/1998 | Bray et al. |
| 5,851,401 A | 12/1998 | Horwitz et al. |
| 5,854,968 A | 12/1998 | Horwitz et al. |
| 6,127,527 A | 10/2000 | Geerlings |
| 6,153,154 A | 11/2000 | Egorov et al. |
| 6,232,353 B1 | 5/2001 | Alexandratos et al. |

OTHER PUBLICATIONS

Bond, et al., "Nuclear Separations for Radiopharmacy: The Need for Improved Separations to Meet Future Research and Clinical Demands", *Ind. Eng. Chem. Research*, (2000) 39:3130–3134, no month.
Whitlock, et al., "Radionuclide Therapy for the Treatment of Microscopic Ovarian Carcinoma: An Overview", *Ind. Eng. Chem. Research* (2000) 39:3135–3139, no month.
Hassfjell, et al., "The Development of the α–Particle Emitting Radionuclides $^{212}$Bi and $^{213}$Bi and Their Decay Chain Related Radionuclides, for Therapeutic Applications", *Chem. Rev.* (2001) 101:2019–2036, no month.

Imam, "Advancements in Cancer Therapy with Alpha–Emitters: A Review", *Int. J. Radiation Oncology Biol. Phys.* (2001) 51:271–278, no month.
McDevitt, et al., "Tumor Therapy with Targeted Atomic Nanogenerators", *Science* (2001) 294:1537–1540, no month.
Gansow, et al., *Radionuclide Generators: New Systems for Nuclear Medicine Applications*, F.F. Knapp, Jr. and T.A. Butler, eds., American Chemical Society: Washington, DC 1984, pp. 215–227, no month.
Dietz, et al., "Improved Chemistry for the Production of Yttrium–90 for Medical Applications", *Appl. Radiat. Isol.* (1992) 43:1093–1101, no month.
Mirzadeth, et al., "Biomedical Radioisotope Generator Systems", *J. Radioanal. Nucl. Chem.* (1996) 203:471–488, no month.
Lambrecht, et al., "Radionuclide Generators", *Radiochim. Acta* (1997) 77:103–123, no month.
Wu, et al., "An Improved Generator for the Production of $^{213}$Bi and $^{225}$Ac", *Radiochem. Acta.* (1997) 79:141–144, no month.
Jurisson, et al., "Coordination Compounds in Nuclear Medicine", *Chem. Rev.* (1993) 93:1137–1156, no month.
Schwochau, "Technetium Radiopharmaceuticals–Fundamentals, Synthesis, Structure, and Development", *Angew. Chem. Int. Ed. Engl.* (1994) 33:2258–2267, no month.
Anderson, et al., "Radiometal–Labeled Agents (Non–Technetium) for Diagnostic Imaging", *Chemical Rev.* (1999), 99:2219–2234, no month.
Diamond, et al., "Resin Selectivity in Dilute to Concentrated Aqueous Solutions" Chapter 8 in *Ion Exchange: A Series of Advances, vol. 1*, J.A. Marinsky, ed., Marcel Dekker, Inc. (Buffalo, New York: 1966) pp. 277–351, no month.
Bray, et al., "Development of a Unique Bismuth (Bi–213) Automated Generator for Use in Cancer Therapy", *Ind. Eng. Chem. Res.* (2000) 39:3189–3194, no month.
Logsdail, et al., *Solvent Extraction in the Process Industries*, vol. 3, Proceedings of ISEC 1993, Elsevier Applied Science (London: 1993), pp. 1641–1648, no month.

(List continued on next page.)

*Primary Examiner*—Steven Bos
(74) *Attorney, Agent, or Firm*—Welsh & Katz, Ltd.

(57) ABSTRACT

A multicolumn selectivity inversion generator has been developed in which bismuth-213 is selectively extracted from an HCl solution of the actinium-225 parent (and its radiogenic descendents) by a primary separation column containing a separation medium containing a neutral oxygenated organophosphorus extractant. After rinsing with dilute HCl, the bismuth-213 is stripped with a buffered NaCl solution. The stripped solution is passed through a cation-exchange resin guard column that retains the actinium-225 and radium-225 contaminants while the bismuth-213 elutes. This generator method minimizes the unpredictable effects of radiation damage to the support material and permits the reliable production of bismuth-213 of high chemical and radionuclidic purity.

28 Claims, 19 Drawing Sheets

OTHER PUBLICATIONS

Mirzadeh, "Generator–produced Alpha–emitters", *Appl. Radiat. Isol.* (1998) 49:345–349, no month.

Molinski, "A Review of $^{99m}$Tc Generator Technology", *Int. J. Appl. Radiat. Isol.* (1982) 33:811–819, no month.

Dietz, et al., *Metal Ion Separation and Preconcentration: Progress and Opportunities, vol. 716*; Bond et al., eds., American Chemical Society: (Washington, DC: 1999), pp. 234–250, no month.

Boyd, "Molybdenum–99: Technetium–99m Generator", *Acta.* (1982) 30:123–145, no month.

Horwitz, et al., "DIPEX: A new extraction chromatographic material for the separation and preconcentration of actinides from aqueous solution", *React. Funct. Polymers*, 33:25–36 (1997), no month.

Horwitz, et al., "Separation and Preconcentration of Strontium from Biological, Environmental, and Nuclear Waste Samples by Extraction Chromatography Using a Crown Ether", *Anal. Chem.* (1991) 63:522–525, no month.

Sekine, et al., *Solvent Extraction Chemistry*, Marcel Kekker (New York: 1977), no month.

Massart, *Nuclear Science Series, Radiochemical Techniques: Cation–Exchange Techniques in Radiochemistry*, NAS–NS 3113 National Academy of Sciences (1971), December.

Schulz et al., eds., "Synthesis, Properties, Reactions and Analysis," in *Science and Technology of Tributyl Phosphate, vol. 1*, CRC Press (Boca Raton, Florida: 1984), no month.

Rydberg, et al. *Principles and Practices of Solvent Extraction*, Marcel Dekker (New York: 1992), no month.

Conventional Generator

Multicolumn Selectivity Inversion Generator

DAAP

PRODUCTION OF ULTRAPURE BISMUTH-213 FOR USE IN THERAPEUTIC NUCLEAR MEDICINE

CROSS REFERENCE TO RELATED APPLICATIONS

This application claims priority from U.S. provisional applications Ser. No. 60/372,327 filed Apr. 12, 2002 and Ser. No. 60/300,141 filed Jun. 22, 2001.

TECHNICAL FIELD

This invention relates to the separation of a daughter radionuclide from its parental radionuclides in the preparation of highly purified radionuclides for use in medicinal treatments, and more particularly to the preparation of an aqueous solution of highly purified bismuth-213(III) ions from solution containing radioactive parental ions such as actinium-225(III) and radium-225(II).

BACKGROUND ART

The use of radioactive materials in diagnostic medicine has been readily accepted because these procedures are safe, minimally invasive, cost effective, and they provide unique structural and/or functional information that is otherwise unavailable to the clinician. The utility of nuclear medicine is reflected by the more than 13 million diagnostic procedures that are performed each year in the U.S. alone, which translates to approximately one of every four admitted hospital patients receiving a nuclear medical procedure. [See, Adelstein, et al., Eds., *Isotopes for Medicine and the Life Sciences*; National Academy Press: Washington, D.C., 1995; Wagner et al., "Expert Panel: Forecast Future Demand for Medical Isotopes", Department of Energy, Office of Nuclear Energy, Science, and Technology; 1999; and Bond et al., *Ind. Eng. Chem. Res.* 2000, 39:3130–3134.]

The use of radiation in disease treatment has long been practiced, with the mainstay external beam radiation therapy now giving way to more targeted delivery mechanisms. By example, sealed-source implants containing palladium-103 or iodine-125 are employed in the brachytherapeutic treatment of prostate cancer; samarium-153 or rhenium-188 are conjugated to diphosphonate-based biolocalization agents that concentrate at metastases in the palliation of bone cancer pain; and radioimmunotherapy (RIT) relies on radionuclide conjugation to peptides, proteins, or antibodies that selectively concentrate at the disease site whereby radioactive decay imparts cytotoxic effects.

Radioimmunotherapy represents the most selective means of delivering a cytotoxic dose of radiation to diseased cells while sparing healthy tissue, [see, Geerlings et al., U.S. Pat. No. 5,246,691, 1993; Whitlock et al., *Ind. Eng. Chem. Res.* 2000, 39:3135–3139; Hassfjell et al., *Chem. Rev.* 2001, 101:2019–2036; Imam, *Int. J. Radiation Oncology Biol. Phys.* 2001, 51:271–278; and McDevitt et al., *Science* 2001, 294:1537–1540] and the plethora of information about disease genesis and function arising from the human genome project is expected to propel RIT into a leading treatment for micrometastatic carcinoma (e.g., lymphomas and leukemias) and small- to medium-sized tumors.

Candidate radionuclides for RIT typically have radioactive half-lives in the range of 30 minutes to several days, coordination chemistry that permits attachment to biolocalization agents, and a high linear energy transfer (LET). The LET is defined as the energy deposited in matter per unit path length of a charged particle, [see, Choppin et al., *Nuclear Chemistry: Theory and Applications*; Pergamon Press: Oxford, 1980] and the LET of α-particles is substantially greater than $\beta^{1-}$-particles. By example, α-particles having a mean energy in the 5–9 MeV range typically expend their energy within about 50–90 $\mu$m in tissue, which corresponds to several cell diameters. The lower LET $\beta^{1-}$-particles having energies of about 0.5–2.5 MeV can travel up to 10,000 $\mu$m in tissue, and the low LET requires as many as 100,000 $\beta^{1-}$-emissions at the cell surface to afford a 99.99 percent cell-kill probability. For a single α-particle at the cellular surface, however, the considerably higher LET gives a 20–40 percent probability of inducing cytotoxicity as the lone α-particle traverses the nucleus. [See, Hassfjell et al., *Chem. Rev.* 2001, 101:2019–2036.]

Because of their use in medical procedures, various governing bodies [e.g., the U.S. Food and Drug Administration (FDA)] mandate rigorous purity requirements for radiopharmaceuticals. Regulations governing the use of radionuclides for therapeutic applications are even more stringent, and such strict regulation is not unexpected given the greater potential harm posed by long-lived high LET radionuclidic impurities. Manufacturers that can ensure the production of therapeutically useful radionuclides with the following three characteristics are at a significant advantage entering the FDA review process and, subsequently, in the deployment of their products in the medical technology markets: (1) high radionuclidic purity; (2) high chemical purity; and (3) predictable radionuclide generator behavior.

The need to ensure high radionuclidic purity stems directly from the hazards associated with the introduction of long-lived or high energy radioactive impurities into a patient, especially if the biolocalization and body clearance characteristics of the radioactive impurities are unknown. Radionuclidic impurities pose the greatest threat to patient welfare, and such contaminants are the primary focus of clinical quality control measures that attempt to prevent the administration of harmful, and potentially fatal, doses of radiation to the patient.

Chemical purity is vital to a safe and efficient medical procedure because the radionuclide must generally be conjugated to a biolocalization agent prior to use. This conjugation reaction typically relies on the principles of coordination chemistry wherein an illustrative cationic radionuclide is chelated to a ligand that is covalently attached to a biolocalization agent. In a chemically impure sample, the presence of ionic impurities can inhibit this conjugation reaction resulting in a substantial quantity of radionuclide not bound to the biolocalization agent. Therapeutic radionuclides not associated with a biolocalization agent not only pose a health concern if administered, but represent an inefficient use of both the radionuclide and the costly biolocalization agent.

Given the preeminent position of technetium-99m ($^{99m}$Tc) in diagnostic nuclear medicine and the simple and effective operation of the conventional $^{99m}$Tc generator (FIG. 1), the logic and design of this radionuclide generator have become the industry standard for nuclear medicine. This conventional radionuclide generator is widely used in diagnostic nuclear medicine where the decay schemes involve less energetic radionuclides and, subsequently, radiolytic degradation of the support matrix is inconsequential.

Conversely, radiotherapeutic nuclides have a high LET that causes significant damage to the support material that is used in the purification process and is therefore responsible for the purity of the product. The adverse effects from radiation damage have frequently been observed with radiotherapeutic nuclides [see, Hassfjell et al., *Chem. Rev.* 2001, 101:2019–2036; Gansow et al., in *Radionuclide Generators: New Systems for Nuclear Medicine Applications*, Knapp, Jr. et al. Eds., American Chemical Society: Washington, D.C., 1984, pp 215–227; Knapp, F. F., Jr.; Butler, T. A., Eds. *Radionuclide Generators: New Systems for Nuclear Medicine Applications*; American Chemical Society: Washington, D.C., 1984; Dietz et al., *Appl. Radiat. Isot.* 1992, 43:1093–1101; Mirzadeh et al., *J. Radioanal. Nucl. Chem.* 1996, 203:471–488; Lambrecht et al., *Radiochim. Acta* 1997, 77:103–123; and Wu et al., *Radiochim. Acta* 1997, 79:141–144] and can degrade the generator performance and separation efficiency to a point where patient safety is compromised.

The same LET that makes $\alpha$- and $\beta^{1-}$-emitting nuclides potent cytotoxic agents for cancer therapy also introduces many unique challenges into the production and purification of these radionuclides for use in medical applications. Foremost among these challenges is the radiolytic degradation of the support material that occurs when the conventional generator methodology of FIG. 1 is used with high LET radionuclides. [See, Hassfjell et al., *Chem. Rev.* 2001, 101:2019–2036; Gansow et al., in *Radionuclide Generators: New Systems for Nuclear Medicine Applications*; Knapp, Jr. et al. Eds., American Chemical Society: Washington, D.C., 1984, pp 215–227; Knapp, F. F., Jr.; Butler, T. A., Eds. *Radionuclide Generators: New Systems for Nuclear Medicine Applications*; American Chemical Society: Washington, D.C., 1984; Dietz et al., *Appl. Radiat. Isot.* 1992, 43:1093–1101; Mirzadeh et al., *J. Radioanal. Nucl. Chem.* 1996, 203:471–488; Lambrecht et al., *Radiochim. Acta* 1997, 77:103–123; and Wu et al., *Radiochim. Acta* 1997, 79:141–144.] Radiolytic degradation of the generator support material can result in: (1) compromised radionuclidic purity (e.g., the support material may release parent radionuclides to the eluate: termed "breakthrough"); (2) diminished chemical purity (e.g., radiolysis products from the support matrix may contaminate the daughter solution); (3) low yields of daughter radionuclides (e.g., $\alpha$-recoil could force the radionuclides into stagnant regions of the support making them less accessible to the stripping eluent); (4) decreases in column flow rates (e.g., fragmentation of the support matrix may create fine particles that clog the chromatographic bed); and (5) erratic performance (e.g., variability in product purity, non-reproducible yields, fluctuating flow rates, and the like).

As discussed above, the use of high LET $\alpha$- and $\beta^{1-}$-emitting radiation holds great promise for the therapy of micrometastatic carcinoma and certain tumor masses, but realization of the full potential of targeted radiotherapy requires the development of ample supplies and reliable generators for high LET radionuclides. [See, Geerlings et al., U.S. Pat. No. 5,246,691, 1993; Whitlock et al., *Ind. Eng. Chem. Res.* 2000, 39:3135–3139; Hassfjell et al., *Chem. Rev.* 2001, 101:2019–2036; Imam, *Int. J. Radiation Oncology Biol. Phys.* 2001, 51:271–278; and McDevitt et al., *Science* 2001, 294:1537–1540.] One candidate $\alpha$-emitter proposed for use in cancer therapy is bismuth-213 ($^{213}$Bi), [see, Geerlings et al., U.S. Pat. No. 5,246,691, 1993; Hassfjell et al., *Chem. Rev.* 2001, 101:2019–2036; and Imam, *Int. J. Radiation Oncology Biol. Phys.* 2001, 51:271–278], which forms as part of the uranium-233 ($^{233}$U) decay chain shown in FIG. 2.

The commercial deployment of $^{213}$Bi is expected to involve shipment of the 10.0 day half-life $^{225}$Ac parent to the nuclear pharmacy for use as the generator source material. Examination of FIG. 3 shows that $^{225}$Ra, with a half-life of 14.9 days, also appears to be a suitable source material for use in the nuclear pharmacy; however, trace $^{224}$Ra arising from $^{233}$U nucleogenesis side reactions contaminates the $^{225}$Ra. Radium-224 introduces very unfavorable radionuclidic contaminants that collectively prohibit the use of $^{225}$Ra as the source material. Actinium-225 is a unique member of the $^{225}$Ra decay chain and does not appear as a $^{224}$Ra daughter, and thus $^{225}$Ac represents the best source material for the production of $^{213}$Bi in the nuclear pharmacy. Key radionuclidic impurities in the production of $^{213}$Bi include the relatively long-lived $^{225}$Ac parent and, to a lesser extent, the trace $^{225/224}$Ra that could potentially arise from inefficient separations of $^{225}$Ac from $^{225/224}$Ra and $^{229/228}$Th.

After separation from its radiogenic relatives in the nuclear pharmacy, the $^{213}$Bi is typically conjugated to a biolocalization agent using coordination chemistry alluded to previously. The cyclic and acyclic polyaminocarboxylates are among the most widely used chelating moieties tethered to biolocalization agents [see, Hassfjell et al., *Chem. Rev.* 2001, 101:2019–2036; Jurisson et al., *Chem. Rev.* 1993, 93:1137–1156; Schwochau, *Angew. Chem. Int. Ed. Eng.* 1994, 33:2258–2267; and Anderson et al., *Chem. Rev.* 1999, 99:2219–2234] and, consequently, the pH range 4–8 is preferred to promote efficient radioconjugation and to minimize chemical attack (e.g., denaturation, hydrolysis, etc.) of the biolocalization agent. An ideal generator would thus produce $^{213}$Bi in dilute acid or in a physiologically acceptable buffer solution that does not contain ligands that can interfere with the radioconjugation reaction such as $I^{1-}$, chelating agents, and the like.

With an understanding that the radionuclide generator requires an initial separation of a hard Lewis acid $Ac^{3+}$ ion from a soft Lewis acid $Bi^{3+}$ ion, the differing Lewis acidities and the concomitant difference in stabilities of the halide ion complexes of $Ac^{3+}$ and $Bi^{3+}$ provides a chemical means to be exploited for the separation. By example, the logarithm of the overall complex formation constants (log $\beta_{MHL}$) for $BiCl_4^{1-}$ is log $\beta_{104}$=6.4 at $\mu$=1.0 and 25° C., whereas only the log $\beta_{101}$=–0.1 is reported for the formation of $AcCl^+$ and $CeCl^+$. [See, Martell et al., "Critically Selected Stability Constants of Metal Complexes: Database Version 4.0," NIST; Gaithersburg, Md., 1997.]

Given the similarity in the weak complex formation constants of the first $Cl^{1-}$ complexes (i.e., log $\beta_{101}$) of $Ac^{3+}$ and $Ce^{3+}$ and the approximate similarity in their six-coordinate ionic radii (i.e., $Ce^{3+}$=1.01 Å and $Ac^{3+}$=1.12 Å) [see, Shannon, *Acta Crystallogr., Sect. A* 1976, 32:751–767], $Ce^{3+}$ was used as a chemical analog for $Ac^{3+}$ in the initial stages of generator development discussed hereinafter. Cerium-139 also possesses a $\gamma$-emission that permits direct assay, rather than relying on the characteristic 218 keV $\gamma$-emission of $^{221}$Fr to indirectly monitor $^{225}$Ac behavior. (The preponderance of $\alpha$- and $\beta^{1-}$-emissions of the $^{225}$Ac daughters makes liquid scintillation (LSC) counting impractical for these studies.)

The propensity of Bi(III) to form stable anionic complexes with halide ions suggests that anion-exchange resins or membranes can be effective for the separation of $BiX_4^{1-}$ ($X=Cl^{1-}$, $Br^{1-}$, or $I^{1-}$) from Ac(III), [see, Diamond et al., in *Ion Exchange*; Marinsky Ed., Marcel Dekker: New York, 1966, Vol. 1, pp 277–351] and several authors have utilized such an approach. [See, Hassfjell et al., *Chem. Rev.* 2001, 101:2019–2036; Bray et al., U.S. Pat. No. 5,749,042, 1998; Egorov et al., U.S. Pat. No. 6,153,154, 2000; and Bray et al., *Ind. Eng. Chem. Res.* 2000, 39:3189–3194.] Recent studies have employed anion-exchange membranes in a manual $^{213}$Bi(III) purification technology [see, Bray et al., U.S. Pat. No. 5,749,042, 1998; and Bray et al., *Ind. Eng. Chem. Res.* 2000, 39:3189–3194] that was subsequently automated. [See, Egorov et al., U.S. Pat. No. 6,153,154, 2000.]

Those membrane technologies relied on the use of a single anion-exchange membrane to retain $^{213}$Bi(III) from 0.5 M HCl, while passing its radiogenic relatives. After a gas flush of the membrane and its associated housing, as much as 2–3 percent of the $^{225}$Ac(III) parent remained and was necessarily removed by a 0.005 M HCl rinse. Because of the low acid concentration, this rinse solution containing $^{225}$Ac(III) could not be directed to the $^{225}$Ac(III) source vessel, and resulted in a net depletion of $^{225}$Ac from the generator system. The $^{213}$Bi(III) was subsequently stripped from the anion-exchange membrane using 0.1 M NaOAc at pH=5.5, which eluted only 88 percent of the $^{213}$Bi(III) in 4 mL of strip solution. The volume of solution in which the $^{213}$Bi(III) was recovered in these tests is near the upper limit of acceptability, as the subsequent radioconjugation reactions and other operations that precede clinical administration typically dilute the $^{213}$Bi even further, resulting in a low specific radioactivity sample.

The radionuclidic purity of the $^{213}$Bi purified using the above-described anion-exchange membrane technology is poor, with a reported decontamination factor (DF) of $^{213}$Bi from $^{225}$Ac of only about 1400. This DF corresponds to about 21 μCi (or 4.7×10$^7$ disintegrations per minute) of $^{225}$Ac contaminating a single 30 mCi patient dose of $^{213}$Bi. Such a quantity of the long-lived $^{225}$Ac parent is unacceptable from patient safety and dosimetry considerations, and the poor DF ultimately leads to unacceptable losses of $^{225}$Ac that shorten the $^{213}$Bi generator duty cycle.

An alternative separation to conventional anion exchange centers on the observation that the BiX$_4^{1-}$ anion can be extracted from hydrohalic acid aqueous phases into a variety of polar diluents [see, Rogers et al., in *Solvent Extraction in the Process Industries, Proceedings of ISEC '93*; Logsdail et al. Eds., Elsevier Applied Science: London, 1993, Vol. 3, pp 1641–1648] and into solvents containing neutral organophosphorus extractants (i.e., phosphine oxides, phosphinates, phosphonates, and phosphates). [See, Sekine et al., *Solvent Extraction Chemistry*; Marcel Dekker: New York, 1977.] By example, solvent extraction using tri-n-butyl phosphate has been shown to partition [H$_3$O][TcO$_4$] (TcO$_4^{1-}$ is a large polarizable anion resembling BiX$_4^{1-}$) to the organic phase and various platinum group metal halides (e.g., PdCl$_4^{2-}$) have been extracted by various alkylphosphine oxide organic phases.

The thermodynamic drivers for BiX$_4^{1-}$ extraction from dilute hydrohalic acid media into neutral organophosphorus extractant systems involve: (1) the salvation of the hydronium cation (H$_3$O$^+$) by hydrogen-bonding interactions with the strongly Lewis basic phosphoryl oxygen donors of the neutral organophosphorus extractants and (2) the salvation preferences of the BiX$_4^{1-}$ anion that encounters a more thermodynamically favorable salvation environment in the polar organic phase. In practice, stripping of Bi(III) from such systems can be accomplished by raising the pH value (i.e., consuming H$_3$O$^+$) and/or by increasing the halide concentration leading to formation of BiX$_5^{2-}$ and/or BiX$_6^{3-}$ complexes that report to the aqueous phase.

The above anionic membrane technology notwithstanding, bismuth-213 is presently obtained for use by elution from a conventional generator in which the relatively long-lived (i.e., 10.0 day) actinium-225 ($^{225}$Ac) parent is retained on an organic cation-exchange resin, while the $^{213}$Bi is eluted with HCl [see, Geerlings et al., U.S. Pat. No. 5,246,691, 1993; Lambrecht et al., *Radiochim. Acta* 1997, 77:103–123; and Mirzadeh, *Appl. Radiat. Isot.* 1998, 49, 345–349] or mixtures of Cl$^-$ and I$^-$. [See, Geerlings et al., U.S. Pat. No. 5,246,691, 1993; Lambrecht et al., *Radiochim. Acta* 1997, 77:103–123; Mirzadeh, *Appl. Radiat. Isot.* 1998, 49, 345–349; Geerlings, U.S. Pat. No. 5,641,471, 1997; and Geerlings, U.S. Pat. No. 6,127,527, 2000.]

This generator strategy suffers from the adverse effects of radiolytic degradation outlined above, and the use of I$^{1-}$ to facilitate effective stripping inhibits the conjugation of $^{213}$Bi to biolocalization agents. The Bi—I bond possesses considerable covalent character and the complex formation constants for I$^{1-}$ complexes of Bi$^{3+}$ are large, [see, Martell et al., "Critically Selected Stability Constants of Metal Complexes: Database Version 4.0," NIST; Gaithersburg, Md., 1997] suggesting that I$^{1-}$ can effectively compete with the polyaminocarboxylate chelating moieties of the biolocalization agent. In order for $^{213}$Bi to be successfully deployed in cancer therapy, new generator technologies are needed to enable the reliable production of $^{213}$Bi of high radionuclidic and chemical purity.

A variety of organic sorbents, most notably the conventional cation- and anion-exchange resins, have been proposed for use in nuclear medicine generators [see, Gansow et al., in *Radionuclide Generators: New Systems for Nuclear Medicine Applications*, Knapp, Jr. et al. Eds., American Chemical Society: Washington, D.C., 1984, pp 215–227; Mirzadeh et al., *J. Radioanal. Nucl. Chem.* 1996, 203:471–488; Lambrecht et al., *Radiochim. Acta* 1997, 77:103–123; Geerlings, U.S. Pat. No. 5,641,471, 1997; Geerlings, U.S. Pat. No. 6,127,527, 2000; and Molinski, *Int. J. Appl. Radiat. Isot.* 1982, 33:811–819] due to the well documented chemical selectivity [see, Diamond et al., in *Ion Exchange*, Marinsky, J. A., Ed.; Marcel Dekker: New York, 1966; Vol. 1, pp 277–351; and Massart, "Nuclear Science Series, Radiochemical Techniques: Cation-Exchange Techniques in Radiochemistry," NAS-NS 3113; National Academy of Sciences; 1971] and the widespread availability of these materials.

Unfortunately, organic-based ion-exchange resins frequently fail or are severely limited in applications using the conventional generator logic depicted in FIG. 1, and typically do so at radiation levels far below those needed for therapeutic use. By example, polystyrene divinylbenzene copolymer-based cation-exchange resins are used in a generator for the α-emitter $^{212}$Bi, but such materials are limited to approximately two-week duty cycles for 10–20 mCi generators. Radiolytic degradation of the chromatographic support, primarily by the high LET α radiation, reportedly leads to diminished flow rates, reduced $^{212}$Bi yields, and breakthrough of the $^{224}$Ra parent. [See, Mirzadeh et al., *J. Radioanal. Nucl. Chem.* 1996, 203:471–488.] Similarly, a $^{213}$Bi generator employing an organic cation-exchange resin was limited to a shelf life of approximately one week at an activity level of 2–3 mCi of the α-emitting $^{225}$Ac parent. [See, Mirzadeh et al., *J. Radioanal. Nucl. Chem.* 1996, 203:471–488 and Lambrecht et al., *Radiochim. Acta* 1997, 77:103–123.]

Over time, this conventional generator gave reduced yields of $^{213}$Bi, poor radionuclidic purity, and unacceptably slow column flow rates. [See, Mirzadeh et al., *J. Radioanal. Nucl. Chem.* 1996, 203:471–488 and Lambrecht et al., *Radiochim. Acta* 1997, 77:103–123.] The useful deployment lifetime of the $^{213}$Bi generator as well as the amount of $^{213}$Bi activity that can be produced is severely limited by the support materials suitable for use with the conventional generator methodology. [See, Hassfjell et al., *Chem. Rev.* 2001, 101:2019–2036; and Mirzadeh, *Appl. Radiat. Isot.* 1998, 49:345–349.]

Inorganic materials have been used in α-particle generators and are not immune to radiolytic degradation. Several early versions of the α-emitting $^{212}$Bi generator [see, Gansow et al., in *Radionuclide Generators: New Systems for Nuclear Medicine Applications*, Knapp, Jr. et al. Eds., American Chemical Society: Washington, D.C., 1984, pp 215–227; and Mirzadeh, *Appl. Radiat. Isot.* 1998, 49:345–349] used inorganic titanates to retain the long-lived thorium-228 parent, from which the radium-224 ($^{224}$Ra) daughter elutes and is subsequently sorbed onto a conventional cation-exchange resin. Over time the titanate support succumbed to radiolytic degradation, creating fine particulates that forced separations to be performed at elevated pressures.

The so-called hybrid sorbents can be subdivided into extraction chromatographic materials and engineered inorganic ion-exchange materials. Most of the published applications of hybrid materials have used extraction chromatography, whereas the preparation and use of engineered inorganic materials is a more recent phenomenon. Extraction chromatography overcomes the poor ion selectivity and slow partitioning kinetics of inorganic materials by using solvent extraction reagents physisorbed to an inert chromatographic substrate. [See, Dietz et al., in *Metal Ion Separation and Preconcentration: Progress and Opportunities*; Bond et al., Eds., American Chemical Society: Washington, D.C., 1999; Vol. 716, pp 234–250.]

The radiolytic stability of extraction chromatographic supports is improved when the inert substrate is an amorphous inorganic material such as silica, with the most profound results reflected as sustainable flow rates over the generator duty cycle. Such "improved" radiolytic stability is deceptive, however, as the fundamental chemical reactions underlying the parent/daughter separation still involve molecules constructed from an organic framework that remains susceptible to radiolytic degradation. Likewise, organic-based chelating moieties have been engineered into inorganic ion-exchange materials to improve analyte selectivity, but such functionalities continue to suffer the effects of radiolysis.

Preliminary reports using hybrid sorbents as conventional generator supports in the production of $^{213}$Bi have appeared. [See, Hassfjell et al., *Chem. Rev.* 2001, 101:2019–2036; Lambrecht et al., *Radiochim. Acta* 1997, 77:103–123; Wu et al., *Radiochim. Acta* 1997, 79:141–144; and Horwitz et al., U.S. Pat. No. 5,854,968, 1998.] Initial improvements centered on sorption of the $^{225}$Ac parent of $^{213}$Bi on Dipex® Resin, an inert silica-based support to which a chelating diphosphonic acid diester is physisorbed that is available from Eichrom Technologies, Inc., Darien, Ill. The silica substrate exhibits greater radiolytic stability than the previously employed organic resins; however, radiolytic damage (i.e., discoloration) was observed surrounding the narrow chromatographic band in which the $^{225}$Ac parent was loaded, ultimately leading to breakthrough of the $^{225}$Ac parent. [See, Lambrecht et al., *Radiochim. Acta* 1997, 77:103–123; and Wu et al., *Radiochim. Acta* 1997, 79:141–144.]

An incremental improvement in the above generator centered on reducing the radiation density by dispersing the $^{225}$Ac radioactivity over a larger volume of the chromatographic support, which is achieved by loading the Dipex® Resin with $^{225}$Ac in a batch mode rather than in a narrow chromatographic band. [See, Hassfjell et al., *Chem. Rev.* 2001, 101:2019–2036; and Wu et al., *Radiochim. Acta* 1997, 79:141–144.] Unfortunately, this batch loading process is awkward and the Dipex® Resin still suffers from radiolytic degradation of the chelating diphosphonic acid diester upon which the separation efficiency relies.

The ideal radionuclide generator technology should offer operational simplicity and convenience as well as reliable production of near theoretical yields of the desired daughter radionuclide having high chemical and radionuclidic purity. As deployed for diagnostic radionuclides, the conventional generator technology shown in FIG. 1 generally meets several of these criteria, although purity and yield have been observed to fluctuate. [See, Molinski, *Int. J. Appl. Radiat. Isot.* 1982, 33:811–819; and Boyd, *Acta* 1982, 30:123–145.]

The conventional generator is poorly suited to systems involving the high LET radionuclides useful in therapeutic nuclear medicine. The conventional generator methodology is thus not universally acceptable for all radionuclides, especially those targeted for use in therapeutic nuclear medicine. Despite industry preferences for the conventional generator depicted in FIG. 1, the fundamental limitations imposed by radiolytic degradation of the support medium by high LET radioactivity cannot be ignored. The severity of these limitations coupled with the ultimate liability of compromised patient safety argue for the development of alternative generator technologies for therapeutically useful radionuclides.

A shift in the fundamental principles governing generator technologies for therapeutic nuclides is further supported by the fact that the inadvertent administration of the long-lived parents of high LET therapeutic radionuclides would compromise the patient's already fragile health; potentially resulting in death. Because the conventional generator strategy depicted in FIG. 1 relies on long-term storage of the parent radionuclide on a solid support that is constantly subjected to high LET radiation, no assurances can be made regarding the radionuclidic and chemical purity of the daughter radionuclide over a typical 14–60 day generator duty cycle.

The inevitable and unpredictable adverse effects of radiolytic degradation of chromatographic supports by the high LET α-emitting descendents of $^{225}$Ac pose enormous challenges to the development of reliable and efficient $^{213}$Bi radionuclide generators. Any damage to the support material in the conventional generator methodology compromises the separation efficiency, potentially resulting in breakthrough of the parent radionuclides and to a potentially fatal dose of radiation if administered to the patient.

The occurrence of such a catastrophic event can be minimized by the quality control measures integrated into nuclear pharmacy operations, but any lack of safe, predictable generator behavior represents a major liability to the nuclear pharmacy, hospital, and their respective shareholders. The invention described hereinafter provides an alternative technology for the production of $^{213}$Bi using a multicolumn selectivity inversion generator that reliably produces near theoretical yields of $^{213}$Bi of high radionuclidic and chemical purity, minimizes the likelihood of breakthrough of parental radionuclide, and provides for long-term storage of the parent radionuclide separate from the separation media.

BRIEF DESCRIPTION OF THE INVENTION

The present invention contemplates a method for producing a solution of trivalent bismuth-213 daughter radionuclide ions that is substantially free of polyvalent parental cation impurities such as divalent radium-225 and trivalent actinium-225 parental radionuclide ions. A contemplated method comprises the steps of:

contacting an aqueous acidic parent-daughter radionuclide ion solution containing bismuth-213 desired daughter radionuclide ions with a first separation medium having a high affinity for the desired bismuth-213 daughter radionuclide and a low affinity for the parent and other daughter radionuclides. That first separation medium comprises a phosphorus-containing extractant having a phosphoryl bond and the remaining bonds from phosphorus being to one or more of (i) a carbon atom of a $C_1$–$C_{10}$ alkyl group, a benzyl group, a carboxamido $C_1$–$C_6$ alkyl group whose amido nitrogen atom has the formula —$NR^1R^2$ and a phenyl group, (ii) a polymer backbone, (iii) an O—$R^1$ group wherein $R^1$ is a hydrido group (H), a $C_1$–$C_{10}$ alkyl group, a phenyl group or a benzyl group, (iv) a —$NR^1R^2$ group, and (v) a divalent radical selected from the group consisting of an imino group, a $C_1$–$C_{10}$ cyclic or acyclic hydrocarbylene group, a phenylene group and a xylylene group, where each of the $R^1$ and $R^2$ groups is the same or different and is as defined for $R^1$. That contact is maintained for a time period sufficient for the bismuth-213 ions to be bound by the first separation medium to form desired bismuth-213-laden separation medium and a desired daughter-depleted parent-daughter solution.

The desired daughter-depleted parent daughter solution is removed from the separation medium as by elution or decantation.

The desired daughter radionuclide is stripped from the desired daughter-laden separation medium to form an aqueous solution of bismuth-213 ions that may also contain trace quantities of the parent and other daughter radionuclide ions. The solution of trivalent bismuth-213 desired daughter radionuclide ions so formed can be substantially free of divalent radium-225 and trivalent actinium-225 parental radionuclide ion impurities. This stripped solution can be collected (recovered) for further use or directed into another vessel in which the bismuth-213 ions are bound to a biolocalization agent or otherwise reacted to form a desired medicinal preparation.

Thus, in some preferred embodiments, the separation at this stage is sufficient, in that the affinity of the first separation medium is so high for the bismuth-213 and so low for the other parental and daughter ions present that further separation and purification is unnecessary. In other preferred embodiments, a further separation is undertaken. Here, the above-formed aqueous solution of bismuth-213 ions is contacted with a second separation medium that is a polymeric acid cation-exchange resin, preferably a polymeric sulfonic acid, having a high affinity for the parent radionuclide ions and a low affinity for the bismuth-213 desired daughter radionuclide ions. That contact is maintained for a time period sufficient for the parent radionuclide to be bound by the second separation medium to form a solution of trivalent bismuth-213 desired daughter radionuclide that is substantially free of divalent radium-225 and trivalent actinium-225 parental radionuclide ion impurities. The solution so formed can also be collected (recovered) for further use or directed into another vessel in which the bismuth-213 ions are bound or otherwise reacted to form a desired medicinal preparation.

It is preferred that the aqueous solution of radioactive parent and daughters be at about radioactive steady state as ions in solution prior to contacting the first separation medium. It is further preferred that the aqueous solution of bismuth-213 ions obtained from stripping the first separation medium be used unchanged for contacting the second separation medium. It is also preferred that the decontamination factor (DF) of the bismuth-213 desired daughter from the parent radionuclide impurities such as Ra(II) or Ac(III) of each the first and second separation media under the conditions of contact be about $10^2$ or greater (more). Thus, the preferred combined use of the two separation media and contacting conditions can provide a DF of about $10^4$ or greater. A DF value of about $10^4$ or greater can also be achieved using the first separation medium alone.

BRIEF DESCRIPTION OF THE DRAWINGS

In the drawings forming a part of this disclosure.

The present invention has several benefits and advantages.

In one benefit, the method does not require the use of air or gas to separate some of the solutions from one another, which in turn provides better chromatographic operating performance and better overall separation efficiency.

An advantage of a contemplated method is that the separation media have longer useful lifetimes because they tend not to be degraded by radiation due to the relatively short time spent by high linear energy transfer radionuclides in contact with the media.

Another benefit of the invention is that high purity bismuth-213 can be obtained.

Another advantage of the invention is that the high separation efficiency of the separation media permits the bismuth-213 to be recovered in a small volume of eluate solution.

A still further benefit of the invention is that no change in the bismuth-213-containing aqueous solution eluted from the first column is needed prior to contact of that solution with the second separation medium.

A still further advantage of the invention is that the chemical integrity of the separation medium is preserved, which provides a more predictable separation performance and reduces the likelihood of parent radionuclide contamination of the bismuth-213 product.

A still further advantage of the invention is that bismuth-213 of high chemical and radionuclidic purity is obtained.

Still further benefits and advantages will be readily apparent to the skilled worker from the disclosures that follow.

DETAILED DESCRIPTION OF THE INVENTION

The present invention contemplates an improved method for the separation of a desired daughter radionuclide, bismuth-213, from a solution containing its parent radionuclide (actinium-225) and that may also contain other daughter radionuclides (e.g., francium-221, astatine-217, etc.). This method utilizes apparatus shown in FIG. 3 with a procedure that permits radioactive parent and daughters to reach radioactive steady state as ions in solution separate from a column containing a separation medium, and has the profound advantage of minimizing radiolytic degradation of the separation medium that is responsible for product purity because the majority of the radioactive decay energy is deposited in the solution matrix that is most typically aqueous.

The integrity of the separation medium is further maintained by using relatively high chromatographic flow rates (e.g., by an automated fluid delivery system) to minimize the duration of contact between the highly radioactive solution and the chromatographic separation medium that selectively extracts the daughter radionuclide. Preserving the chemical integrity of the separation medium results in more predictable separation performance and reduces the likelihood of parent radionuclides contaminating the daughter product.

Figure 3:
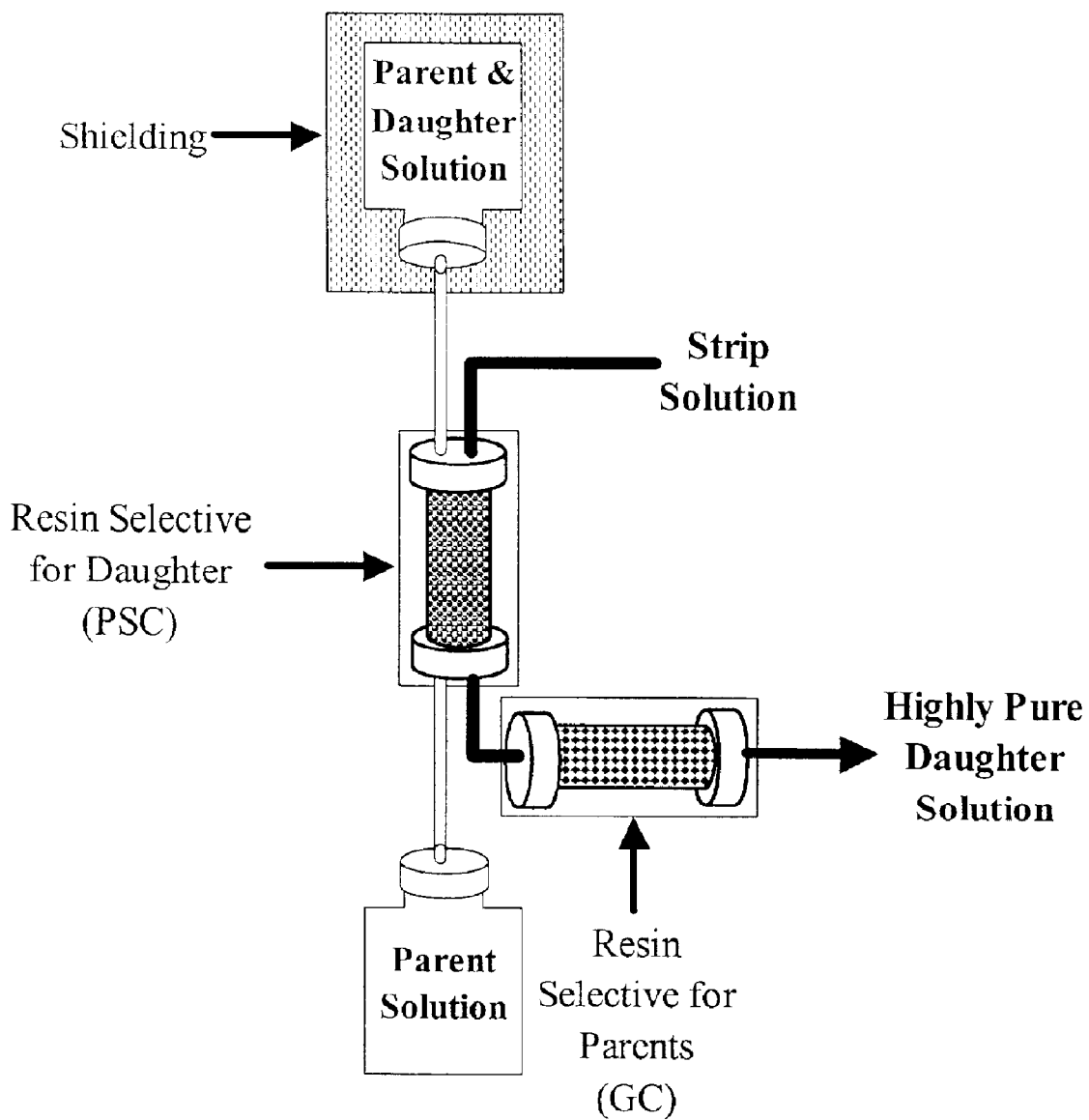
FIG. 3 is a schematic depiction of a multicolumn selectivity inversion generator useful herein. PSC refers to Primary Separation Column and GC refers to Guard Column.

To further minimize the probability of parent radionuclide contamination in some embodiments, a second separation medium selective for the radiogenic parent(s) is provided downstream from the daughter-selective primary separation column, as shown in FIG. 3. The addition of a second separation column (referred to herein as the guard column) can add another dimension of security, ensuring that hazardous long-lived parent radionuclides are not administered to the patient.

Figure 1:
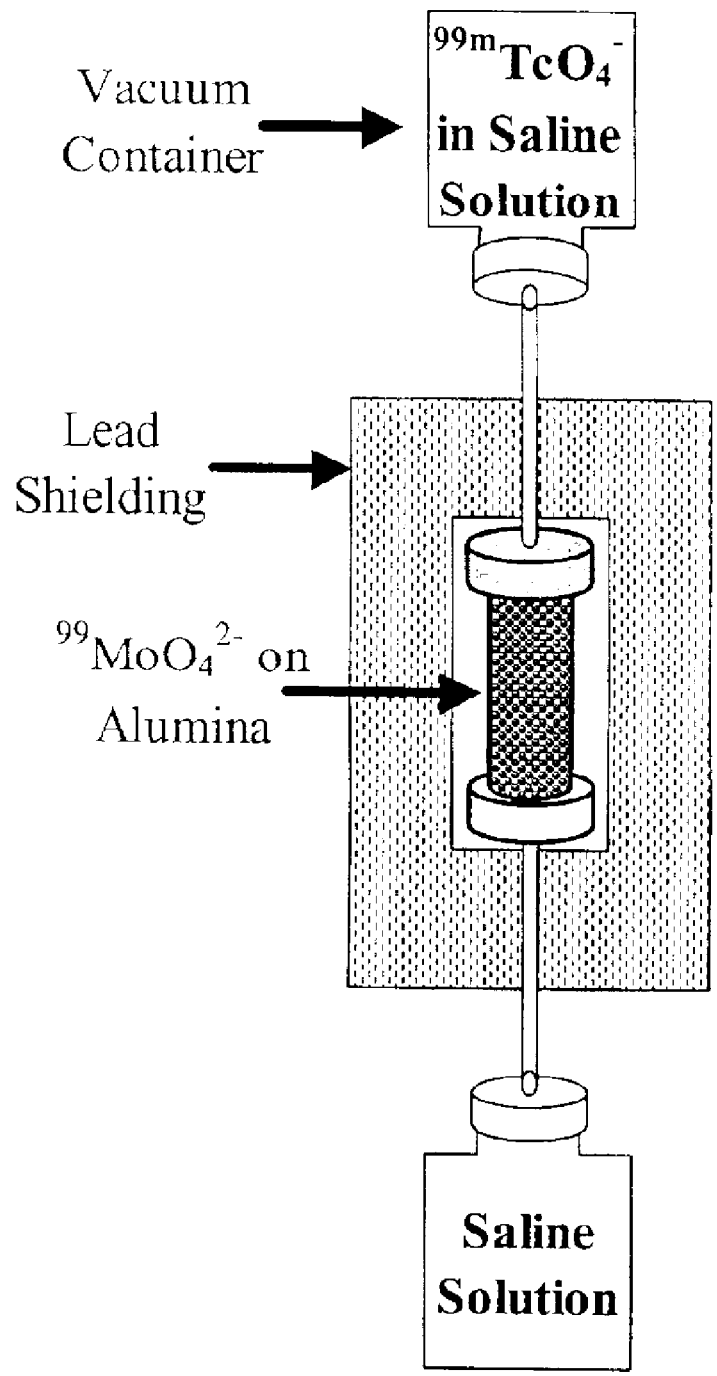
FIG. 1 is a schematic depiction of a conventional generator methodology as deployed for $^{99m}$Tc.

At least two fundamental differences between a preferred multicolumn selectivity inversion generator used in this invention and shown in FIG. 3 and the conventional generator shown in FIG. 1 are: (1) the storage medium for the parent radionuclide(s) is an aqueous solution rather than a solid support and (2) a second separation medium used in some embodiments herein ensures that the parent radionuclide(s) do not exit the generator system.

More specifically, one embodiment of the present invention contemplates the steps of contacting an aqueous acidic parent-daughter radionuclide ion solution containing bismuth-213 desired daughter radionuclide ions with a first separation medium having a high affinity for the desired bismuth-213 daughter radionuclide and a low affinity for the parent and other daughter radionuclides. That first separation medium comprises a phosphorus-containing extractant having a phosphoryl bond and the remaining bonds from phosphorus being to one or more of (i) a carbon atom of a $C_1$–$C_{10}$ alkyl group, a benzyl group, a carboxamido $C_1$–$C_6$ alkyl group whose amido nitrogen atom has the formula —$NR^1R^2$ and a phenyl group, (ii) a polymer backbone, (iii) an O—$R^1$ group wherein $R^1$ is a hydrido group (H), a $C_1$–$C_{10}$ alkyl group, a phenyl group or a benzyl group, (iv) a —$NR^1R^2$ group, and (v) a divalent radical selected from the group consisting of an imino group, a $C_1$–$C_{10}$ cyclic or acyclic hydrocarbylene group, a phenylene group and a xylylene group, where each of the $R^1$ and $R^2$ groups is the same or different and is as defined for $R^1$. That contact is maintained for a time period sufficient for the bismuth-213 ions to be bound by the first separation medium to form a desired bismuth-213-laden separation medium and a desired daughter-depleted parent-daughter solution.

The bismuth-213 desired daughter-depleted parent daughter solution is removed from the separation medium as by elution or decantation.

The desired daughter radionuclide is stripped from the desired daughter-laden separation medium to form an aqueous solution of bismuth-213 ions that may also contain trace quantities of the parent and other daughter radionuclide ions. In some preferred embodiments, the solution of trivalent bismuth-213 desired daughter radionuclide ions so formed can be substantially free of divalent radium-225 and trivalent actinium-225 parental radionuclide ion impurities as well as other daughter radionuclide ions. The stripped solution can therefore be collected (recovered) for further use or directed into another vessel in which the bismuth-213 ions are bound to a biolocalization agent or otherwise reacted to form a desired medicinal preparation.

Thus, in some preferred embodiments, the separation at this stage is sufficient; that is, the affinity of the first separation medium is so high for the bismuth-213 and so low for the other parental and daughter ions present that further separation and purification is unnecessary. In other preferred embodiments, a further separation is undertaken.

Where the further separation is undertaken, the above-formed aqueous solution of bismuth-213 ions is contacted with a second separation medium that is a polymeric acid cation-exchange resin, preferably a polymeric sulfonic acid, having a high affinity for the parent radionuclide ions and a low affinity for the bismuth-213 desired daughter radionuclide ions. That contact is maintained for a time period sufficient for the parent radionuclide to be bound by the second separation medium to form a solution of trivalent bismuth-213 desired daughter radionuclide that is substantially free of divalent radium-225 and trivalent actinium-225 parental radionuclide ion impurities, as well as other daughter radionuclide ion impurities. The solution so formed can also be collected (recovered) for further use or directed into another vessel in which the bismuth-213 ions are bound or otherwise reacted to form a desired medicinal preparation.

Thus, taking the two stage separation as illustrating both the use of one column and the use of two column separations, the aqueous acidic solution containing the parental and bismuth-213 desired daughter radionuclide ions is contacted with a first separation medium having a high affinity for the desired bismuth-213 daughter radionuclide and a low affinity for the parent and other daughter radionuclides. The solution typically is in a hydrohalide acid such as hydrochloric, hydrobromic or hydroiodic acids. Hydrochloric acid is preferred because the other acids, while useful, have anions that can interfere with subsequent processing to the separated bismuth-213, resulting in unnecessary loss of bismuth-213 due to radioactive decay. The acid concentration is about 0.02 to about 0.4 M, and preferably at about 0.1 M, so that the $D_w$ value for the utilized separation medium at the selected contact pH value is about 100-fold ($10^2$) or more greater for Bi(III) than for Ac(III) and Ra(II).

A contemplated separation can typically accommodate a concentration of parent and daughter radionuclides of up to about $10^{-3}$ molar (1 mM). In usual practice, concentrations of such radionuclides of about $10^{-11}$ M to about $10^{-4}$ M are utilized, with concentrations of about $10^{-9}$ M to about $10^{-6}$ M being more preferred.

A separation medium having a high affinity for one ion and a low affinity for another is typically described as a function of decontamination factors for the separation medium and parent and daughter ions under the solution conditions of the contacting. An individual separation medium in a column utilized provides a decontamination factor (DF) of the bismuth-213 desired daughter from the parent radionuclide impurities likely to be present such as Ra(II) or Ac(III) of about $10^1$ or greater (more) under the conditions of contacting. A typical DF value is more usually about $10^2$ to about $10^5$ or greater, under the conditions of contacting. The decontamination factor, its definition and calculation are discussed hereinafter.

The separation media used herein are preferably themselves polymeric or based on a polymer that is coated with extractant molecules. These polymers are preferably particulate. Many separation medium particles are generally spherical in shape and exhibit consistent size and morphology. Other separation particles are irregularly shaped and non-spherical. Both particle types are often referred to as resin beads, or more simply as beads. Sheets, webs, fibers or other solid forms of separation medium can also be used. The first separation medium is preferably present in a chromatography column referred to herein as a primary separation column.

The first separation medium is a phosphorus-containing extractant containing a phosphoryl bond (group). A contemplated extractant is often referred to in the art as a neutral oxygenated organophosphorus extractant. Although a preferred extractant contains a single phosphoryl bond, many preferred extractants contain two or more phosphoryl groups.

A phosphoryl bond or phosphoryl group contains one phosphorus atom and one oxygen atom. Illustrative separation media contain neutral oxygenated organophosphorus-containing extractants that include a phosphinic, phosphonic, or phosphoric acid, ester or amide group as well as a phosphine oxide or diphosphine oxide group. Thus, illustrative extractants can be a phosphine oxide (including a diphosphine oxide), phosphinate, phosphonate, or phosphate. The phosphoryl bond is sometimes portrayed as P=O, and at other times as $P^+$—$O^-$. Either depiction is suitable for the present invention.

The remaining bonds from phosphorus are to one or more of (i) a carbon atom of a $C_1$–$C_{10}$ alkyl group, a benzyl group, a carboxamido $C_1$–$C_6$ alkyl group whose amido nitrogen atom has the formula —$NR^1R^2$ and a phenyl group, (ii) a polymer backbone, (iii) an O—$R^1$ group wherein $R^1$ is a hydrido group (H), a $C_1$–$C_{10}$ alkyl group, a phenyl group or a benzyl group, (iv) a —$NR^1R^2$ group, and (v) a divalent radical selected from the group consisting of an imino group, a $C_1$–$C_{10}$ cyclic or acyclic hydrocarbylene group, a phenylene group and a xylylene group, where each of the $R^1$ and $R^2$ groups is the same or different and is as defined for $R^1$.

The first separation medium is water-insoluble, as is the second separation medium discussed hereinafter. Where the first separation medium is comprised of a particulate material such as a polymer that is coated with a phosphoryl group-containing extractant, that extractant is also water-insoluble. Thus, although an above-described phosphorus-containing extractant can have one or more bonds from phosphorus to substituent groups such as hydrido and $C_1$–$C_{10}$ alkyl groups, several of the substituent groups bonded to phosphorus in the extractant are of sufficient hydrophobicity (chain length) that the extractant is water-insoluble.

A material is deemed water-insoluble for purposes of this invention if it has a solubility in water at 25° C. of about five parts in ten thousand (0.05%) or less, and preferably about one part in ten thousand (0.01%) or less, and most preferably about five parts in one hundred thousand or less (0.005%). As an example, tri-n-butylphosphate that is often used along with octyl,phenyl-N,N-diisobutylcarbamoyl-methylphosphine oxide (CMPO), on an inert support for extraction of actinide ions is reported to have a solubility in water at 25° C. of 0.039%. [See, J. A. Riddick and W. B. Bunger, *Organic Solvents, Techniques of Chemistry volume II*, Wiley-Interscience, New York (1970) page 323.]

One preferred separation medium is commercially available from Eichrom Technologies, Inc., located at 8205 S. Cass Avenue, Darien, Ill., under the mark UTEVA®. The UTEVA® Resin is 40 percent dipentyl pentylphosphonate (DAAP) extractant on 50–100 μm Amberchrom®-CG71. Another preferred separation medium also available from Eichrom Technologies, Inc. is sold under the trademark UTEVA®-2 Resin and contains an equimolar mixture of Cyanex®-923 extractant (a mixture of n-alkyl phosphine oxides available from Cytec Industries, Inc., West Paterson, N.J.) and DAAP loaded to 40 percent on 50–100 μm Amberchrom®-CG71. The components of Cyanex®-923 are understood to include trihexylphosphine oxide, trioctylphosphine oxide, as well as dihexyloctylphosphine oxide and dioctylhexylphosphine oxide.

A separation medium referred to as TOPO Resin that corresponds to 20 percent (w/w) loading of 0.25 M tri-n-octylphosphine oxide (TOPO) extractant in n-dodecane on Amberchrom®-CG71 is also useful herein.

Octyl,phenyl-N,N-diisobutylcarbamoyl-methylphosphine oxide, known in the art as CMPO, can also be used in a separation medium. The CMPO extractant can be dissolved in tri-n-butyl phosphate and coated on an inert resin bead to provide a useful separation medium. The use of CMPO is discussed in U.S. Pat. Nos. 4,548,790, No. 4,574,072 and No. 4,835,107.

Some of the above phosphine oxide compounds contain one phosphoryl group and three bonds from phosphorus to carbon atoms of $C_1$–$C_{10}$ alkyl groups, whereas DAAP is a phosphonate that contains one phosphoryl bond, one phosphorus to alkyl carbon atom bond and two bonds between phosphorus and the oxygen atoms of an O—$R^1$ groups. On the other hand, CMPO is a phosphine oxide that contains a phosphoryl bond, one bond between phosphorus and a $C_1$–$C_{10}$ alkyl group, one bond between phosphorus and a phenyl group, and a bond between phosphorus and a carboxamido $C_1$–$C_6$ alkyl group whose amido nitrogen atom has the formula—N$R^1R^2$.

Exemplary separation media in which the phosphoryl group-containing extractant phosphorus atom is bonded to a polymer backbone includes resins based on a styrene-divinyl benzene polymer matrix that includes phosphonic, and/or gem-diphosphonic acid functional groups or their esters chemically bonded thereto and can also include sulfonic acid functionalities. One such gem-diphosphonic acid resin is commercially available from Eichrom Technologies, Inc., under the name Diphonix® resin. In the present process, the Diphonix® resin is used in the H⁺ form. The characteristics and properties of Diphonix® resin are more fully described in U.S. Pat. Nos. 5,539,003, 5,449,462 and 5,281,631.

Another polymeric separation medium contains monophosphonic acid or diphosphonic acid (DPA) extractant ligands or groups. Several types of DPA-containing substituted diphosphonic acids are known in the art and can be used herein. An exemplary diphosphonic acid ligand has the formula

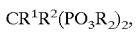

wherein R is selected from the group consisting of hydrogen (hydrido), a $C_1$–$C_8$ alkyl group, a cation, and mixtures thereof;

$R^1$ is hydrogen or a $C_1$–$C_2$ alkyl group; and $R^2$ is hydrogen or a bond to a polymeric resin.

When $R^2$ is a bond to a polymeric resin, the phosphorus-containing groups are present at 1.0 to about 10 mmol/g dry weight of the copolymer and the mmol/g values are based on the polymer where $R^1$ is hydrogen. Exemplary exchange media containing diphosphonic acid ligands are discussed hereinbelow.

Illustrative polymeric diphosphonic acid separation media are discussed in U.S. Pat. Nos. 5,281,631, 5,449,462, 5,539, 003, and No. 5,618,851. An illustrative monophosphonic acid separation medium is discussed in U.S. Pat. No. 6,232, 353 B1.

Another useful separation medium is Diphosil™ resin. Similar to the other DPA resins, Diphosil™ resin contains a plurality of geminally substituted diphosphonic acid ligands such as those provided by vinylidene diphosphonic acid. The ligands are chemically bonded to an organic matrix that is grafted to silica particles. Diphosil™ resin is available from Eichrom Technologies, Inc.

Where $R^2$ is hydrido in the above formula $CR^1R^2(PO_3R_2)_2$, the exchange medium contains a non-polymeric extractant that is usually applied as a surface coating (i.e., physisorbed) to polymeric beads. One such separation medium is referred to as Dipex® Resin, which is an extraction chromatographic material containing a liquid diphosphonic acid extractant belonging to a class of diesterified methanediphosphonic acids, such as di-2-ethylhexyl methanediphosphonic acid. The extractant is sorbed on a substrate that is inert to the mobile phase such as Amberchromo®-CG71 (available from TosoHaas, Montgomeryville, Pa.) or hydrophobic silica. In this extractant, $R^1$ and $R^2$ are H and one R is 2-(ethyl)-hexyl and the other is H.

The active component of a preferred Dipex® resin is a liquid diphosphonic acid extractant of the general formula,

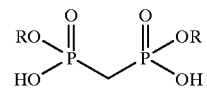

where R is $C_6$–$C_{18}$ alkyl or aryl, and preferably an ester derived from 2-ethyl-1-hexanol. A preferred compound is P,P'-bis-2-(ethyl)hexyl methanediphosphonic acid. Dipex® Resin [40 percent P,P'-bis(2-ethylhexyl)-methanediphosphonic acid on 20–50 μm Amberchrom®-CG71] is available from Eichrom Technologies, Inc. Acrylic and polyaromatic resins such as AMBERLITE®, commercially available from Rohm and Haas Company of Philadelphia, Pa., can also be used.

The properties and characteristics of Dipex® Resin are more fully described in Horwitz et al. U.S. Pat. No. 5,651, 883 and Horwitz et al. U.S. Pat. No. 5,851,401, as well as in Horwitz et al., *React. Funct. Polymers*, 33:25–36 (1997).

The above mono- and diphosphonic acid-containing separation media each contain a phosphoryl group, with the remaining bonds to phosphorus being between phosphorus and a polymer backbone, phosphorus and a $C_1$–$C_{10}$ alkyl group or between phosphorus and a O—$R^1$ group.

A still further useful phosphoryl bond-containing neutral oxygenated organophosphorus extractant is a diphosphine oxide. Exemplary diphosphine oxide compounds correspond in structure to the formula

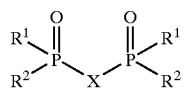

wherein $R^1$ and $R^2$ are the same or different and are as defined before, and X is a divalent radical selected from the group consisting of an imino group (—NH—), a divalent $C_1$–$C_{10}$ cyclic or acyclic hydrocarbyl group [e.g. hydrocarbylene such as an alkylene (methylene, ethylene), alkenylene (propenylene; —CH$_2$CH=CH$_2$—) or alkynylene (butynlene; —CH$_2$C CCH$_2$—)], a phenylene (—C$_6$H$_4$—) group or a xylylene (—CH$_2$C$_6$H$_4$CH$_2$—) group]. Illustrative diphosphine oxides include P,P'-dimethyl P,P'-diphenyl methylene-diphosphine oxide and P,P,P'P'-tetraphenyl ethylenediphosphine oxide.

The contact between the aqueous acidic parent-daughter radionuclide ion solution is maintained for a time period sufficient for the bismuth-213 ions to be bound by the first separation medium to form a desired bismuth-213-laden separation medium and a desired daughter-depleted parent-daughter solution. The time of contact between a solution and a separation medium is typically the residence time of passage of the solution through a column of separation medium under whatever pressure head is utilized, although gravity flow is acceptable. Thus, although one can admix a given solution and separation medium and maintain the contact achieved there between for a period of hours or days, sorption (extraction) of the bismuth-213 (III) ions by the separation medium is usually rapid enough, that is, the binding and phase transfer reactions are sufficiently rapid, that contact provided by flow over and through the separation medium particles provides sufficient contact time to effect a desired separation.

Extraction of the bismuth-213 desired daughter ions from the solution by the separation medium forms bismuth-213 desired daughter-laden separation medium. That extraction of the bismuth-213 from the solution also forms a desired daughter-depleted parent-daughter solution.

The desired daughter-depleted parent-daughter solution is removed from the separation medium. That removal can be accomplished by decantation or pouring, and is more usually accomplished by elution of the resulting desired daughter-depleted parent-daughter solution from the column of the primary separation medium. The removed solution is typically separately maintained in an appropriately shielded container to permit the formation of further amounts of bismuth-213.

The bismuth-213 desired daughter radionuclide is removed from the desired daughter-laden separation medium to form an aqueous solution of bismuth-213 ions. This removal step is usually referred to in the art as stripping.

The stripping step can be accomplished using a number of solutions, but it is preferred to strip with a solution that contains buffer salts that can be administered to a patient. It is also preferred that the stripping solution be at a pH value near that which can be administered to a patient or used for conjugation of the $^{213}$Bi(III) ions to peptides or proteins such as antibody molecules for use in radioimmunotherapy or the like. Thus, for example, the first separation medium can be stripped of its bismuth-213 ions using 0.1 M NaOAc at pH=5.5, but it is preferred to use a salt solution buffered at a pH value of about 3 to about 7, and more preferably about 3.5 to about 5.5. More preferably, the stripping solution contains about 0.75 M NaCl in an about 0.50 M (Na,H)OAc sodium acetate buffer solution at pH=4.0, or 0.75 M NH$_4$Cl in 0.50 M (NH$_4$,H)OAc buffer (ammonium acetate) solution at pH=4.0.about 0.75 M NaCl in about 0.50 M (Na,H)OAc buffer solution at pH=4.

The aqueous solution of bismuth-213 ions is thereafter contacted with a second separation medium that is preferably in a second column (a guard column). That second separation medium is a polymeric cation-exchange resin having a high affinity for the parent radionuclide and a low affinity of the bismuth-213 desired daughter radionuclide. The second separation medium is again preferably particulate, and more preferably present as generally spherical beads or irregularly shaped beads, as discussed previously for the first separation medium.

For medical purposes, a total DF value of about $10^4$ or greater is usually used. The DF value for a given separation step is multiplied with the DF value for the next step or, when represented using exponents, the DF value exponents are added for each step. Thus, where two separation steps are used, the DF value for the first step can be about $10^1$ or greater and that of the second step about $10^3$ or greater, vice versa, or both at least about $10^2$ or greater. Where the bismuth-213 is not for use in a patient, the first separation step can have a DF value of only about $10^1$.

The difference in affinities of the desired bismuth-213 daughter from the likely parent ions present under the conditions used for the contacting is preferably evidenced by a DF value of about $10^2$ or greater, to about $10^5$ or greater for the primary separation medium. Thus, appropriate pairing of a second guard column of separation medium and separation conditions can afford a combined decontamination factor of desired daughter from parent radionuclide of about $10^4$ or greater, and preferably about $10^6$ or greater, up to about $10^{10}$ or greater, under the conditions of contacting the multiple separation media. A DF value of about $10^{10}$ is about the largest DF that can be readily determined using typical radioanalytical laboratory apparatus.

Sulfonic acid cation-exchange resins are preferred for use in the guard column, and are exemplified by Bio-Rad® AGMP-50 cation-exchange and Eichrom® 50W×8 sulfonic acid cation-exchange resins. Other sulfonic acid cation-exchange resins can also be used such as Amberlite® CG-120, Amberlite® 200 macroreticular resin, Amberlite® IR-120 and IR-130 gel type resins and the Dowex® 50W group of cationic exchange resins. The previously mentioned mono- and diphosphonate (Diphonix®) resins can also be used in the guard column as the second separation medium.

Contact between the second separation medium of the guard column and the aqueous solution of bismuth-213 ions is maintained for a time period sufficient for parent radionuclide that might be present to be bound by the second separation medium to form a solution of trivalent bismuth-213 desired daughter radionuclide that is substantially free of divalent radium-225 and trivalent actinium-225 parental radionuclide impurities. As was previously the case, the contact maintenance time is usually relatively short, being that required to pass the solution over and through the particles of the second separation medium.

In preferred practice, the aqueous solution of bismuth-213 ions formed by stripping the desired daughter ions from the first separation medium is chemically unchanged prior to its being contacted with the second separation medium. That is, the solution goes directly from the column of the first separation medium into the guard column with no additions or subtractions of reagents, nor change in pH value, ion concentration or the like. Thus, using the preferred NaCl/(Na,H)OAc buffer solution at pH=4.0, the recovered bismuth-213 is seamlessly integrated into a radioconjugation reaction involving a biolocalization agent such as a peptide or protein like an antibody. Careful tuning of the separations chemistry to avoid the need for chemically stringent or strongly complexing stripping reagents (e.g., $I^{1-}$) also means that the radioconjugation reactions proceed more rapidly and in higher yields.

As already noted, the separations utilized in a contemplated method from both separation media are typically and preferably carried out using a chromatographic column that contains a solid separation medium; a device well-known to workers in this art. These separations can also be carried out in an open or closed beaker or flask or the like, with solid/liquid separations being carried out by decantation or other method. However, a contemplated method will be discussed herein in terms of column separations because such separations are preferred.

The multicolumn selectivity inversion generator and preparation method described herein can reliably provide near theoretical yields of $^{213}Bi$ of exceptionally high radionuclidic and chemical purity. By minimizing the adverse effects of radiolytic degradation of the support material, this $^{213}Bi$ generator operates at predictably high efficiency over the entire radionuclide generator duty cycle. In addition to exceeding the vital purity criteria, the purified $^{213}Bi$ product is delivered in a small volume of solution. The operational simplicity of the multicolumn selectivity inversion generator for the production-scale purification of $^{213}Bi$ is ideally suited to automation, which is more efficient and reduces the probability of human error to ensure that more patients can be safely treated with $^{213}Bi$ α-particle immunotherapy.

Experimental

All acids were of trace metal grade, and all other chemicals were of ACS reagent grade and used as received. The $^{133}Ba$, $^{139}Ce$, $^{207}Bi$, and $^{226}Ra$ radiotracers were each evaporated to dryness twice in concentrated $HNO_3$ and dissolved in 0.50 M $HNO_3$ prior to use. Samples of $^{225}Ac$ were provided by MedActinium, Inc. of Knoxville, Tenn. and had been separated from $^{229}Th$ supplies at Oak Ridge National Laboratory. MicroCurie quantities of the $^{225}Ac(NO_3)_3$ were thrice dissolved in concentrated HCl and evaporated to dryness before dissolution in 0.10 M HCl for use. The 5 mCi quantity of dry $^{225}Ac(NO_3)_3$ was simply dissolved in 0.10 M HCl prior to use. Standard radiometric assay procedures were employed throughout, and all count rates were corrected for background. The $^{133}Ba$, $^{139}Ce$, and $^{207}Bi$ were monitored using an automated γ counter, and the $^{226}Ra$ was monitored using liquid scintillation counting. The 218 keV peak in the γ-spectrum of $^{221}Fr$ was used to track $^{225}Ac$ behavior, and $^{213}Bi$ was quantified using the 440 keV peak in the γ-spectrum. [See, Lederer et al., Eds. *Table of Isotopes;* 7th ed.; John Wiley and Sons: New York, 1978.]

The extraction chromatographic materials were prepared using a general procedure described previously. [See, Horwitz et al., *Anal. Chem.* 1991, 63:522–525.] A solution of 0.25 M tri-n-octylphosphine oxide (TOPO) in n-dodecane (0.78 g) was dissolved in about 25 mL of ethanol and combined with 50–100 μm Amberchrom®-CG71 resin (3.03 g; available from TosoHaas, Inc., Montgomeryville, Pa.) in about 25 mL of ethanol. The mixture was rotated at room temperature on a rotary evaporator for about 30 minutes after which the ethanol was vacuum-distilled. The resulting solid is referred to as TOPO Resin and corresponds to 20 percent (w/w) loading of 0.25 M TOPO in n-dodecane on Amberchrom®-CG71.

The UTEVA®-2 Resin was prepared in a similar manner, except that this material contains no diluent and the dispersing solvent was methanol rather than ethanol. The UTEVA®-2 Resin contains an equimolar mixture of Cyanex®-923 (a mixture of n-alkyl phosphine oxides available from Cytec Industries, Inc., West Paterson, N.J.) and DAAP loaded to 40 percent on 50–100 μm Amberchrom®-CG71. The components of Cyanex®-923 are understood to include trihexylphosphine oxide, trioctylphosphine oxide, as well as dihexyloctylphosphine oxide and dioctylhexylphosphine oxide. The UTEVA® Resin is 40 percent dipentyl pentyl phosphonate (DAAP) on 50–100 μm Amberchrom®-CG71 and is commercially available from Eichrom Technologies, Inc.

The percent solids for the Bio-Rad® AGMP-50 and the Eichrom® 50W×8 sulfonic acid cation-exchange resins were determined by transferring a portion of the wet resin to a tared vial followed by drying in an oven at 110° C. until a constant mass was achieved. Each gravimetric analysis was performed in triplicate to afford a percent solids of 48.6(±0.3) percent for AGMP-50 and 62.8(±0.6) percent for 50W×8. All resins were stored in tightly capped containers and were not exposed to air for any lengthy period of time to avoid a change in percent solids.

All dry weight distribution ratios ($D_w$) were determined radiometrically by batch contacts of the resins with the desired solutions at 25(±2)° C. The dry weight distribution ratio is defined as:

$$D_w = \left(\frac{A_o - A_f}{A_f}\right)\left(\frac{V}{m_R \cdot (\% \text{ solids}/100)}\right)$$

where $A_0$=the count rate in solution prior to contact with the resin, $A_f$=the count rate in solution after contact with resin, V=volume (mL) of solution in contact with resin, $m_R$=mass (g) of wet resin, and the % solids permits conversion to the dry mass of resin.

The batch uptake studies were performed by adding μL quantities of the respective radiotracers in 0.50 M $HNO_3$ to 1.2 mL of the solution of interest, gently mixing, and removing a 100 μL aliquot for radiometric assay ($A_0$). One mL of the remaining solution (V) was added to a known mass of wet resin ($m_R$) and centrifuged for 1 minute. The mixture was then stirred gently (so that the resin was just suspended in the solution) for 30 minutes, followed by 1 minute of centrifugation and another 30 minutes of stirring. After 1 minute of centrifugation to settle the resin, the solution was pipeted away and filtered through a 0.45 μm PTFE filter to remove any suspended resin particles. A 100 μL aliquot was then taken for radiometric assay ($A_f$). All dry weight distribution ratios are accurate to 5 percent relative uncertainty.

The Decontamination factor (DF) is defined using the following equation:

$$DF = \left(\frac{\frac{[\text{Analyte}]_{\text{effluent}}}{[\text{Impurity}]_{\text{effluent}}}}{\frac{[\text{Analyte}]_{\text{influent}}}{[\text{Impurity}]_{\text{influent}}}}\right)$$

For a system at radioactive steady state (e.g., $^{225}Ac$, $^{225}Ra$ and their daughters including $^{213}Bi$ and its daughters), the denominator is about 1. This means a DF value can be approximated by examining the stripping peak in a chromatogram and dividing the maximum cpm/mL for the analyte (i.e., the desired $^{213}$Bi daughter radionuclide) by the activity of the impurities (i.e. $^{225}$Ac and $^{225}$Ra parents)

Alternatively, the DF can be calculated by taking the ratio of the dry weight distribution ratios ($D_w$) for an analyte and impurity. Assuming the "influent" is at radioactive steady state (making the denominator for DF unity), the ratio of $D_w$ values for analyte/impurity are:

$$DF = \frac{\left(\frac{A_o - A_f}{A_f}\right)^{analyte} / \left(\frac{V}{m_R \cdot (\% \text{ solids}/100)}\right)}{\left(\frac{A_o - A_f}{A_f}\right)^{impurity} / \left(\frac{V}{m_R \cdot (\% \text{ solids}/100)}\right)}$$

which simplifies after cancellation to:

$$DF = \frac{\left(\frac{A_o - A_f}{A_f}\right)^{analyte}}{\left(\frac{A_o - A_f}{A_f}\right)^{impurity}}$$

where $A_o$, $A_f$, V, $m_R$ and % solids are as previously defined. These ratios of activities are proportional to the molar concentrations cited elsewhere in the definition of DF.

All chromatographic studies were performed in a similar manner using the following general procedure. A quantity of the UTEVA®, UTEVA®-2, or AGMP-50 resins was slurry packed into a 1.2 mL capacity Bio-Spin® disposable plastic chromatography column (Bio-Rad Laboratories, Inc.). A porous plastic frit was placed on top of the bed to prevent its disruption during the addition of eluent. Each column was conditioned by eluting at least 5 bed volumes (BV) of the pristine (not previously used, and free of radionuclides) load solution and followed by gravity elution of a solution containing the radionuclides of interest. The columns were subsequently rinsed with equal to or greater than 4 BV of the pristine load solution prior to stripping. Column eluates were collected into tared counting vials, and all volumes were calculated gravimetrically using the respective solution densities.

EXAMPLE 1

Polyvalent Metal Ion Uptake by UTEVA® Resin and TOPO Resin from HCl

Figure 4:
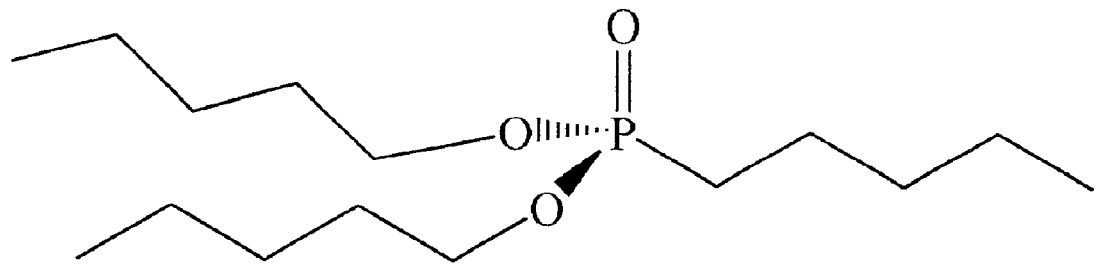
FIG. 4 shows a structural formula for dipentyl pentyl phosphonate (DAAP, the extractant used in UTEVA® Resin).

FIG. 4 shows the structure of dipentyl pentyl phosphonate, DAAP, which is commercially available on an extraction chromatographic material known as UTEVA® Resin. Using the Bi(III) chemistry discussed above, it was hypothesized that [H$_3$O][BiCl$_4$] could be extracted by the DAAP onto UTEVA® Resin and then conveniently stripped by H$_3$O$^+$ consumption and/or an increase in [Cl$^{1-}$]. Proposed loading and stripping equilibria for a UTEVA® Resin primary separation column are presented FIG. 5.

Figure 5:
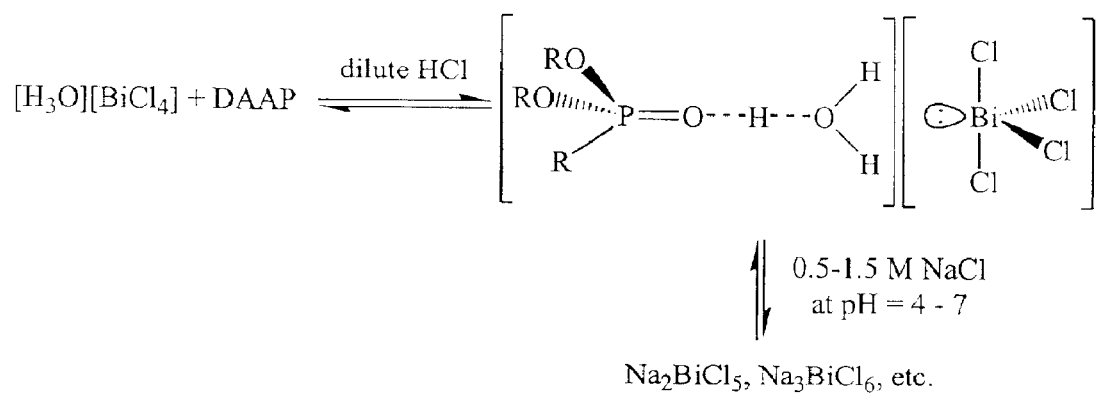
FIG. 5 Shows the principal equilibria involved in the extraction and recovery of Bi(III) from dilute HCl by the DAAP on UTEVA® Resin.

One of several appealing aspects of the separation scheme proposed in FIG. 5 is that extraction of Ra(II) and Ac(III) by chemically pure samples of neutral organophosphorus extractants like DAAP is quite low, [see, Sekine et al., Solvent Extraction Chemistry; Marcel Dekker: New York, 1977; Schulz et al. Eds., Science and Technology of Tributyl Phosphate. Volume I, Synthesis, Properties, Reactions, and Analysis; CRC Press: Boca Raton, Fla., 1984; Vol. I; and Rydberg et al. Eds., Principles and Practices of Solvent Extraction; Marcel Dekker: New York, 1992] suggesting that UTEVA® Resin possesses the selectivity needed for the separation of $^{213}$Bi (III) from $^{225}$Ac(III) and $^{225/224}$Ra(II). Because the solvent extraction of [H$_3$O][BiCl$_4$] is known to vary with the Lewis basicity of the phosphoryl oxygen donor of the neutral organophosphorus extractant (i.e., phosphine oxide>phosphinate>phosphonate>phosphate), [see, Sekine et al., Solvent Extraction Chemistry; Marcel Dekker: New York, 1977; and Rydberg et al. Eds., Principles and Practices of Solvent Extraction; Marcel Dekker: New York, 1992] two different extraction chromatographic resins were examined for their abilities to extract Bi(III) from HCl solutions.

Figure 6:
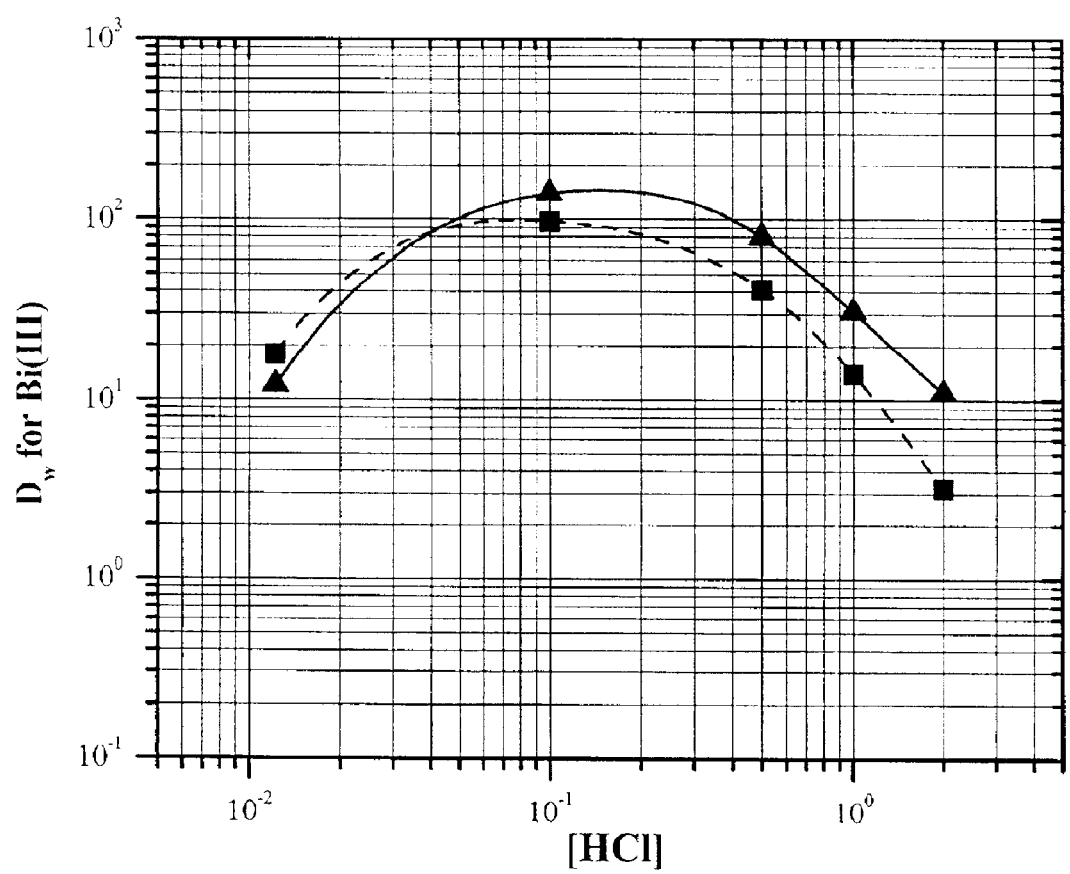
FIG. 6 is a graph that plots $D_w$ values for Bi(III) vs. [HCl] on UTEVA® (closed triangles) and TOPO (closed circles) resins.

The UTEVA® Resin discussed above has diluent-free 40 percent DAAP on an Amberchrom®-CG71 inert support, whereas the TOPO Resin is comprised of 0.25 M tri-n-octylphosphine oxide (TOPO) at 20 percent loading on Amberchrom®-CG71. As shown in FIG. 6, the two resins behave similarly in the extraction of Bi(III) from 0.010–1.0 M HCl. The maximum dry weight distribution ratio ($D_w$) for Bi(III) occurs at 0.10 M HCl with $D_w$=140 exhibited by the UTEVA® Resin. The comparable uptake performance combined with commercial availability favor use of the UTEVA® Resin, and this material became the focus of the remaining studies targeting development of a primary separation column for the isolation of Bi(III).

Figure 2:
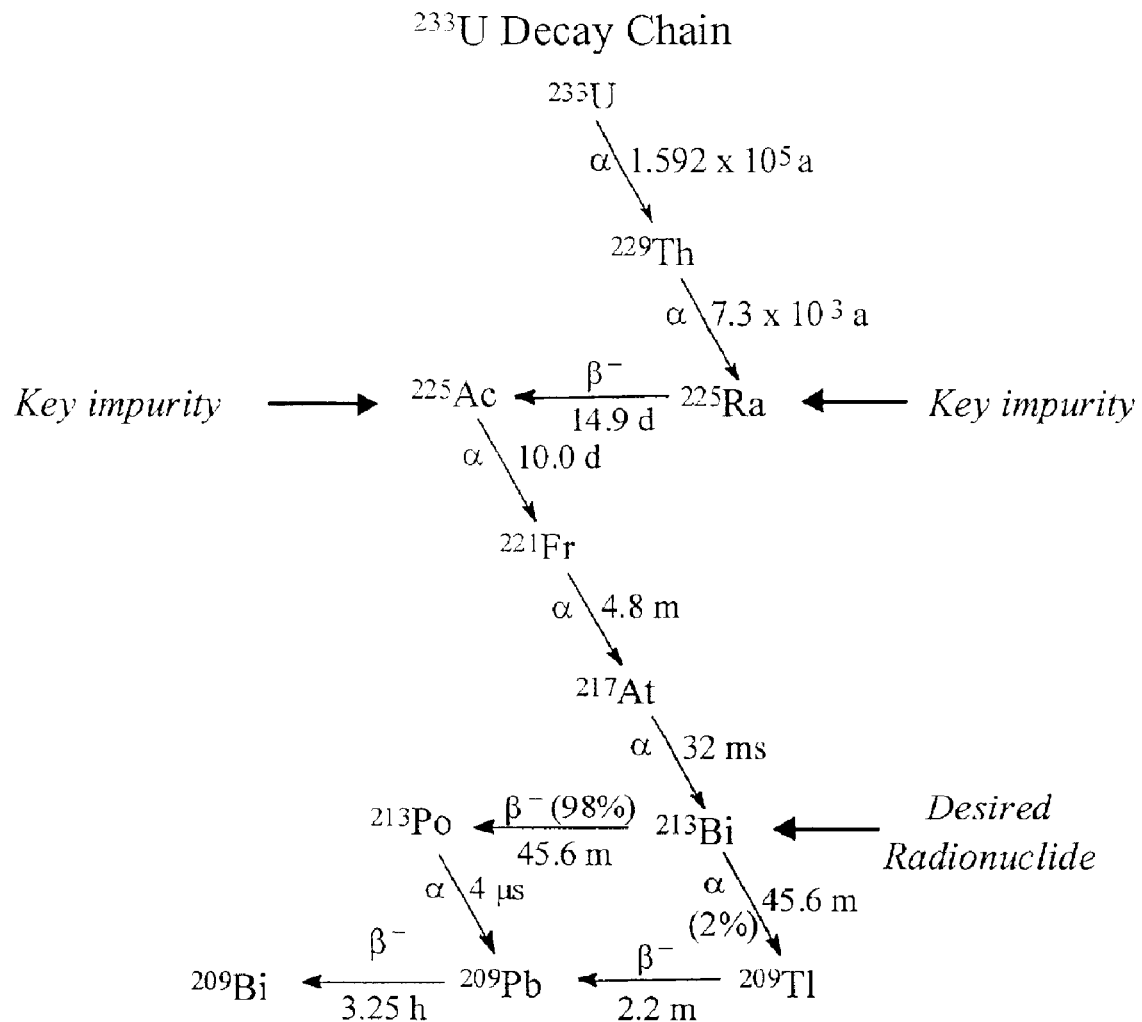
FIG. 2 shows the uranium-233 decay scheme highlighting the key impurities in the development of a multicolumn selectivity inversion generator for $^{213}$Bi.

With the fundamental concept of Bi(III) uptake by UTEVA® Resin established and stripping conditions suggested by FIG. 6 (i.e., [HCl] less than 0.01 M or greater than 2 M), the selectivity of the UTEVA® Resin for Bi(III) over the relevant impurities defined in FIG. 2 was investigated. Based on the reported data for tri-n-butyl phosphate, [see, Sekine et al., Solvent Extraction Chemistry; Marcel Dekker: New York, 1977; Schulz et al. Eds., Science and Technology of Tributyl Phosphate. Volume I, Synthesis, Properties, Reactions, and Analysis; CRC Press: Boca Raton, Fla., 1984; Vol. I; and Rydberg et al. Eds., Principles and Practices of Solvent Extraction; Marcel Dekker: New York, 1992] it was anticipated that the UTEVA® Resin containing DAAP would exhibit effectively no affinity for Ac(III) or Ra(II).

Figure 7:
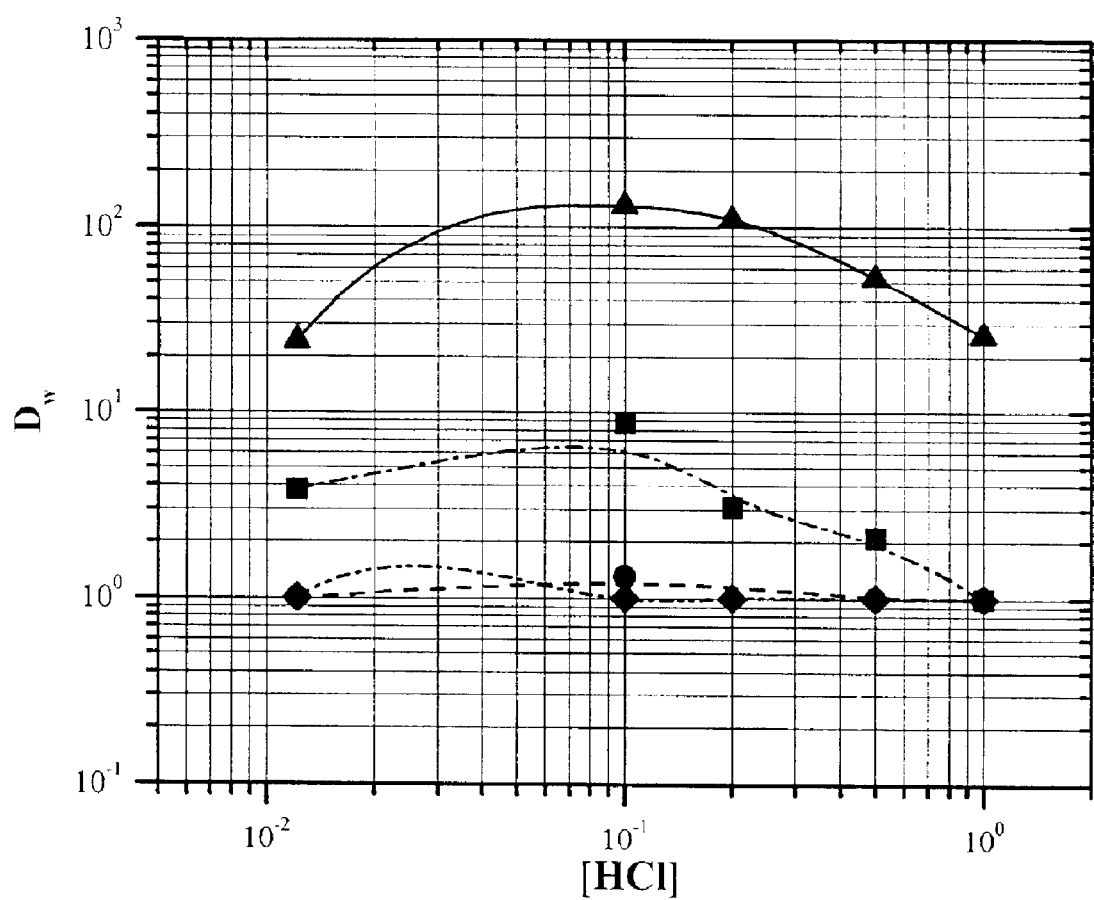
FIG. 7 is a graph that plots $D_w$ values for Ra(II) (closed squares), Ba(II) (closed diamonds), Ce(III) (closed circles), and Bi(III) (closed triangles) vs. [HCl] on UTEVA® Resin.

FIG. 7 shows the $D_w$ values for Ra(II), Ba(II), Ce(III), and Bi(III) on UTEVA® Resin as a function of [HCl]. As shown, the partitioning of Ra(II), Ba(II), and Ce(III) are quite low, with $D_w$ less than 10 in the range 0.010–1.0 M HCl. Note that values of $D_w$ less than 10 obtained from these batch contact studies indicate essentially no sorption; that is, a given analyte is not substantially retained under chromatographic elution conditions.

The $D_w$ value for Bi(III) exhibits a rather broad maximum with $D_w$ greater than 100 in the range 0.05–0.2 M HCl. This plateau is advantageous for commercial production, as Bi(III) uptake is not substantially affected by the minor fluctuations in [HCl] that may arise from α-radiolysis of the storage solution and/or from typical variations in production activities. The DF value of Bi(III) from Ra(II) and Ce(III) (Ac(III)) is about 10$^2$, which suggests the selective separation of $^{213}$Bi(III) by a UTEVA® Resin primary separation column in 0.10 M HCl.

EXAMPLE 2

Separation of Polyvalent Metal Cations in HCl with UTEVA®-2 and UTEVA® Resins

Figure 8:
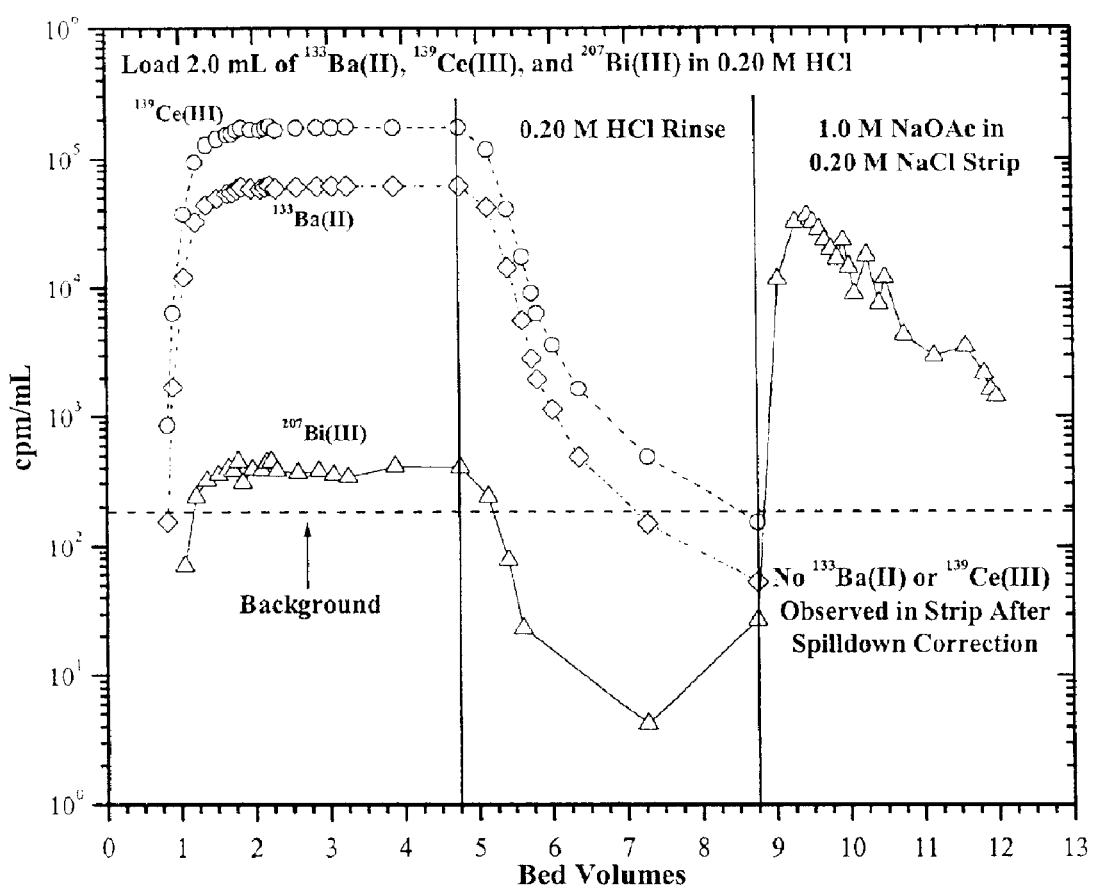
FIG. 8 is a graph that plots cpm/mL vs. bed volumes of eluate for the separation of Ba(II) (open diamonds) and Ce(III) (open circles) from Bi(III) (open triangles) by UTEVA®-2 Resin using 0.20 M HCl as the load and rinse solutions and 1.0 M NaOAc in 0.20 M NaCl as a strip solution.

The results of a chromatographic study are shown in FIG. 8 in which a mixture of $^{122}$Ba(II), $^{139}$Ce(III), and $^{207}$Bi(III), the former two as chemical analogs for Ra(II) and Ac(III), respectively, in 0.20 M HCl were eluted on UTEVA®-2

Resin (a mixture of organophosphine oxides and organophosphonates). During loading of four bed volumes (BV) of 0.20 M HCl, $^{133}$Ba(II) and $^{139}$Ce(III) elute with the first free column volume of eluate. Some $^{207}$Bi(III) was detected during loading, but was not statistically significant at less than twice background radiation levels.

After 3 BV of 0.20 M HCl rinse, the activity of all three analytes reached background levels. Stripping with 1.0 M sodium acetate (NaOAc) in 0.20 M NaCl elutes $^{207}$Bi(III) in a rather broad band, with no significant $^{133}$Ba(II) or $^{139}$Ce(III) activity. This chromatographic study displayed an approximate DF value of $^{213}$Bi(III) from $^{225/224}$Ra(II) and $^{225}$Ac(III) of about $10^3$ using dilute HCl and a neutral organophosphorus extraction chromatographic resin. In addition, stripping of Bi(III) by $H_3O^+$ consumption (i.e., 1.0 M NaOAc has pH=6.5) at a $[Cl^{1-}]$ comparable to that used in loading was demonstrated.

Figure 9:
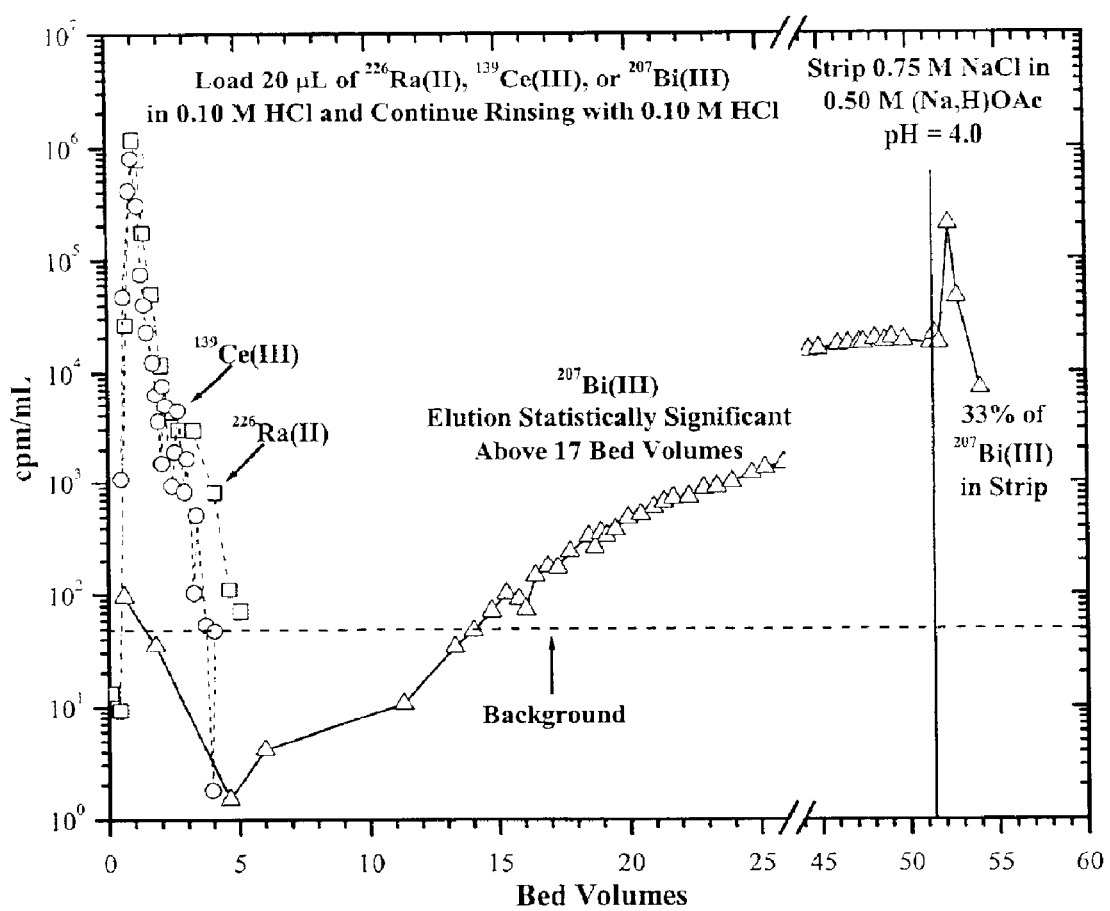
FIG. 9 is a graph that plots cpm/mL vs. bed volumes of eluate for the separation of Ra(II) (open squares) and Ce(III) (open circles) from Bi(III) (open triangles) by UTEVA® Resin in 0.10 M HCl when the chromatographic column was loaded in a narrow chromatographic band, rinsed extensively with 0.10 M HCl, and stripped using a solution of 0.75 M NaCl in 0.50 M sodium acetate [(Na,H)OAc] buffer at pH=4.0.

FIG. 9 shows a different chromatographic study in which $^{207}$Bi(III) was separated from $^{226}$Ra(II) and $^{139}$Ce(III) by the commercially available UTEVA® Resin. Rather than simultaneously loading the activity in 4 BV of 0.20 M HCl, as done for FIG. 8, the $^{226}$Ra(II), $^{139}$Ce(III), and $^{207}$Bi(III) were separately applied to the same column as narrow chromatographic bands in 0.10 M HCl and individually eluted, followed by rinsing. Thus, three separate studies are shown together in FIG. 9. As shown, the $^{226}$Ra(II) and $^{139}$Ce(III) elute immediately (as predicted from the $D_w$ values less than 10, FIG. 7) and reach background radiation levels after 5 BV of rinsing with 0.10 M HCl. After persistent rinsing with 0.10 M HCl, elution of $^{207}$Bi(III) only becomes statistically significant after 17 BV, where the $^{207}$Bi activity eclipses twice background radiation levels. A steady increase in $^{207}$Bi(III) elution continues to about 51 BV of 0.10 M HCl, where the study was truncated and stripping with 0.75 M NaCl in 0.50 M (Na,H)OAc buffer solution at pH=4.0 eluted the remaining 33 percent of the $^{207}$Bi(III).

This study confirms that Bi(III) can be efficiently separated from Ra(II) and Ce(III) using UTEVA® Resin and 0.10 M HCl, and that the retention of Bi(III) by the UTEVA® Resin is sufficient to prevent excessive losses of $^{213}$Bi(III) during the loading and rinsing procedures. In addition, the ability to strip $^{207}$Bi(III) is demonstrated at a higher $[Cl^{1-}]$, a lower pH value, and a lower concentration of (Na,H)OAc buffer solution than used in FIG. 8.

EXAMPLE 3

Guard Column Use to Enhance DF Values

To ensure that no long-lived radionuclidic parents exit the generator system, a guard column was developed to fully realize the advantages of the multicolumn selectivity inversion generator. The extraction equilibria hypothesized in FIG. 5 for the primary separation column are supported by the results of FIGS. 4–7, which provides some insight into the solution speciation of Bi(III) and offers guidance in the selection of guard column materials and solution conditions. It is likely that Bi(III) is present during stripping as a polyanionic complex at $[Cl^{1-}]$ greater than 0.5 M, whereas the $^{225/224}$Ra(II) and $^{225}$Ac(III) impurities exist as neutral ion pairs in solution. These observations suggest that a cation-exchange resin can be used as a guard column, presuming the solution conditions can be tuned to permit elution of bismuth polyhalide anions such as $BiCl_5^{2-}$, $BiCl_6^{3-}$, and the like, from the cation-exchange resin while $^{225/224}$Ra(II) and $^{225}$Ac(III) are retained.

Figure 10:
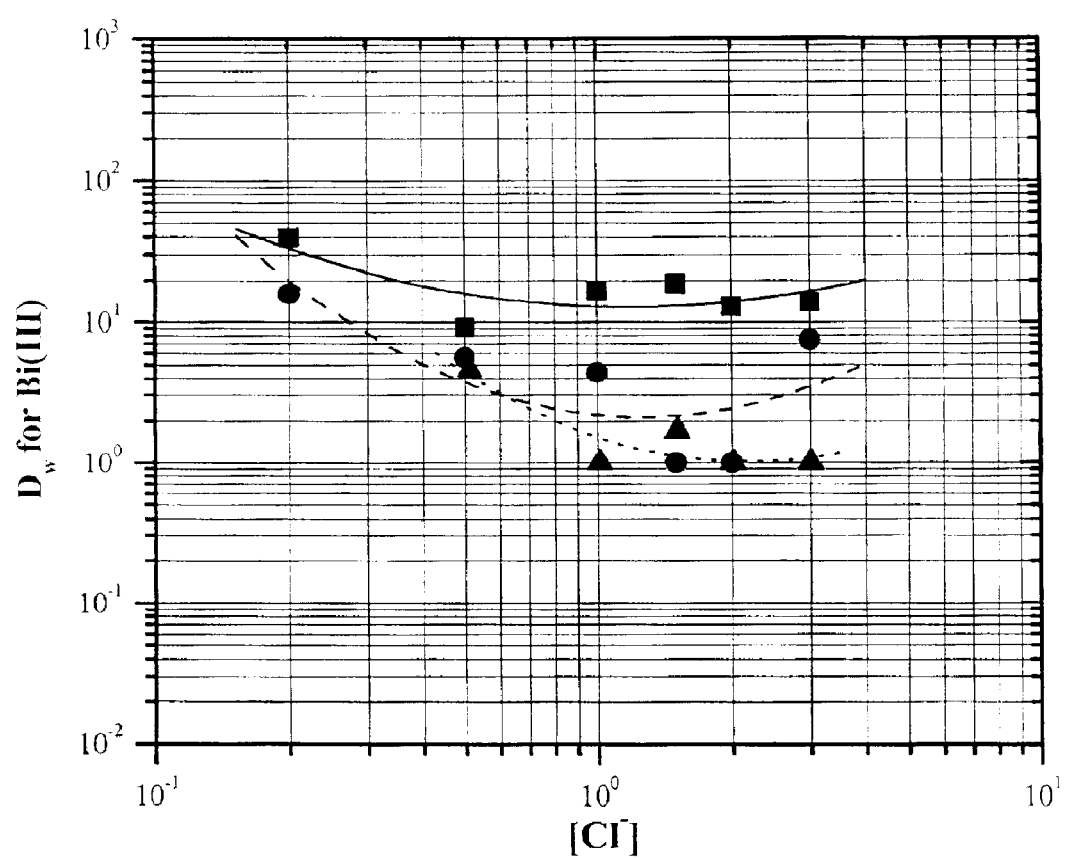
FIG. 10 is a graph of $D_w$ values for Bi(III) vs. [Cl$^-$] on a Bio-Rad® AGMP-50 cation-exchange resin at three different pH values: pH=6.5 (closed squares), pH=4.0 (closed circles) and pH=1.9 (closed triangles).

FIG. 10 shows the variation of $D_w$ values for Bi(III) vs. $[Cl^{1-}]$ on a macroporous sulfonic acid cation-exchange resin, Bio-Rad® AGMP-50, at three different pH values. The mean $D_w$ value for Bi(III) was greater than 10 in 1.0 M NaOAc at pH=6.5, which indicates weak retention of Bi(III) by the AGMP-50 cation-exchange resin. At the lower pH values of 4.0 and 1.9, the $D_w$ values for Bi(III) are all less than 10 in the range 0.50–3.0 M $Cl^{1-}$, indicating no retention of Bi(III).

Although a pH value of 6.5 more closely approaches the physiological pH value (pH 7.2–7.4) desired for radioconjugation reaction and clinical administration, the slight retention of Bi(III) at this pH value reduces yields and can unnecessarily dilute the product because excessive elution volumes are required to recover the $^{213}$Bi(III). At the low end of the acidity spectrum, a solution of pH=1.9 effectively prevents sorption of Bi(III) by the AGMP-50 cation-exchange resin guard column, but this pH value is too acidic for subsequent conjugation reactions and stripping of Bi(III) from the UTEVA® Resin primary separation column is less efficient at this [HCl] (FIG. 7: $D_w$ value for Bi(III)=24). Based on these observations and process knowledge, a solution of 0.50–1.5 M NaCl in a (Na,H)OAc buffer solution at pH=4.0 serves as an effective stripping medium for the UTEVA® Resin primary separation column and minimizes the sorption of Bi(III) by the cation-exchange resin guard column.

Figure 11:
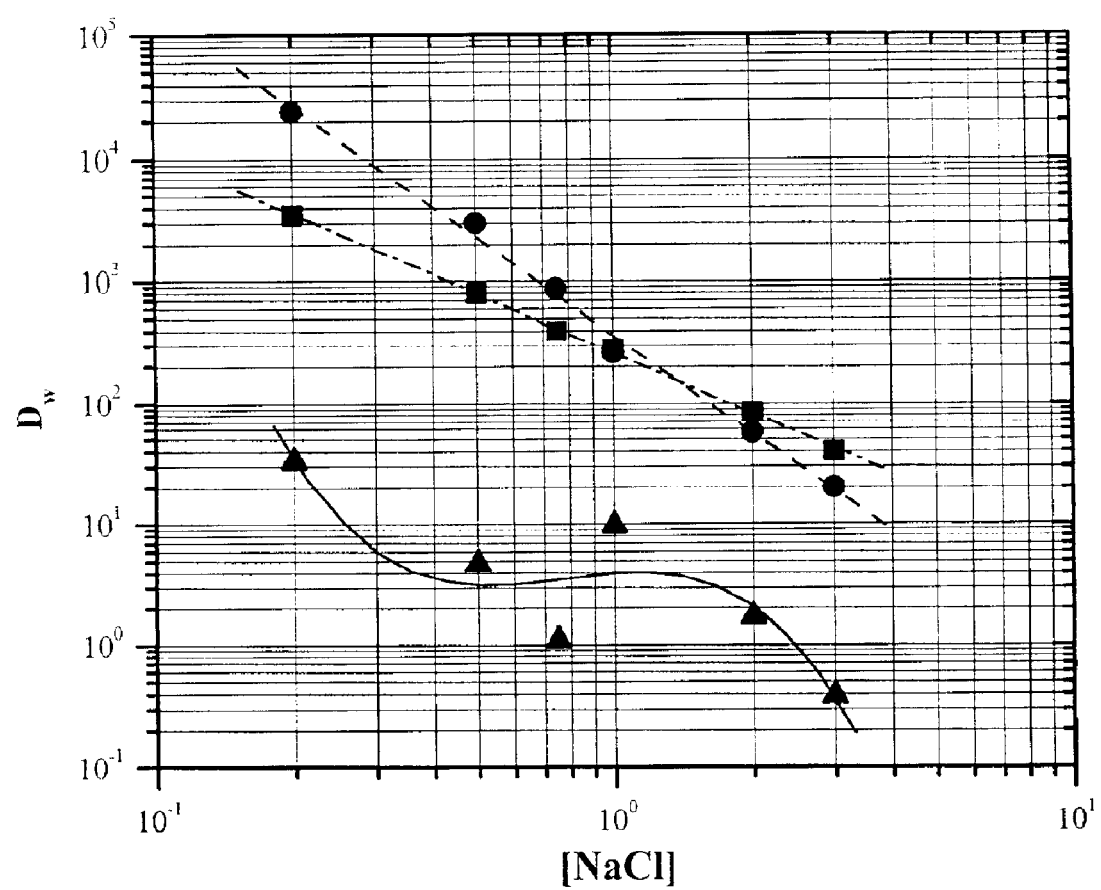
FIG. 11 is a graph of $D_w$ values for Ra(II) (closed squares), Ce(III) (closed circles), and Bi(III) (closed triangles) vs. [NaCl] on 50W×8 cation-exchange resin in 0.50 M (Na,H)OAc buffer at pH=4.0.

The results of FIG. 11 illustrate the variation in $D_w$ value for Ra(II), Ce(III), and Bi(III) vs. [NaCl] in 0.50 M (Na,H)OAc buffer solution at pH=4.0 for Bio-Rad® 50W×8, a conventional gel-type (i.e., not macroporous) sulfonic acid cation-exchange resin. The $D_w$ values for Ra(II) and Ce(III) expectedly decrease linearly as the $[Na^{1+}]$ increases, whereas the $D_w$ value for Bi(III) is less than 10 above 0.50 M NaCl. It is the combined diminution of Ra(II) and Ce(III) [Ac(III)] uptake, the need for efficient elution of Bi(III), and the physiological application that frame the optimal NaCl concentration around 0.75 M. The DF values of Bi(III) from Ra(II) and Ce(III) are about 110 and about 250, respectively, in 0.75 M NaCl in 0.50 M (Na,H)OAc buffer solution at pH=4.0.

Figure 12:
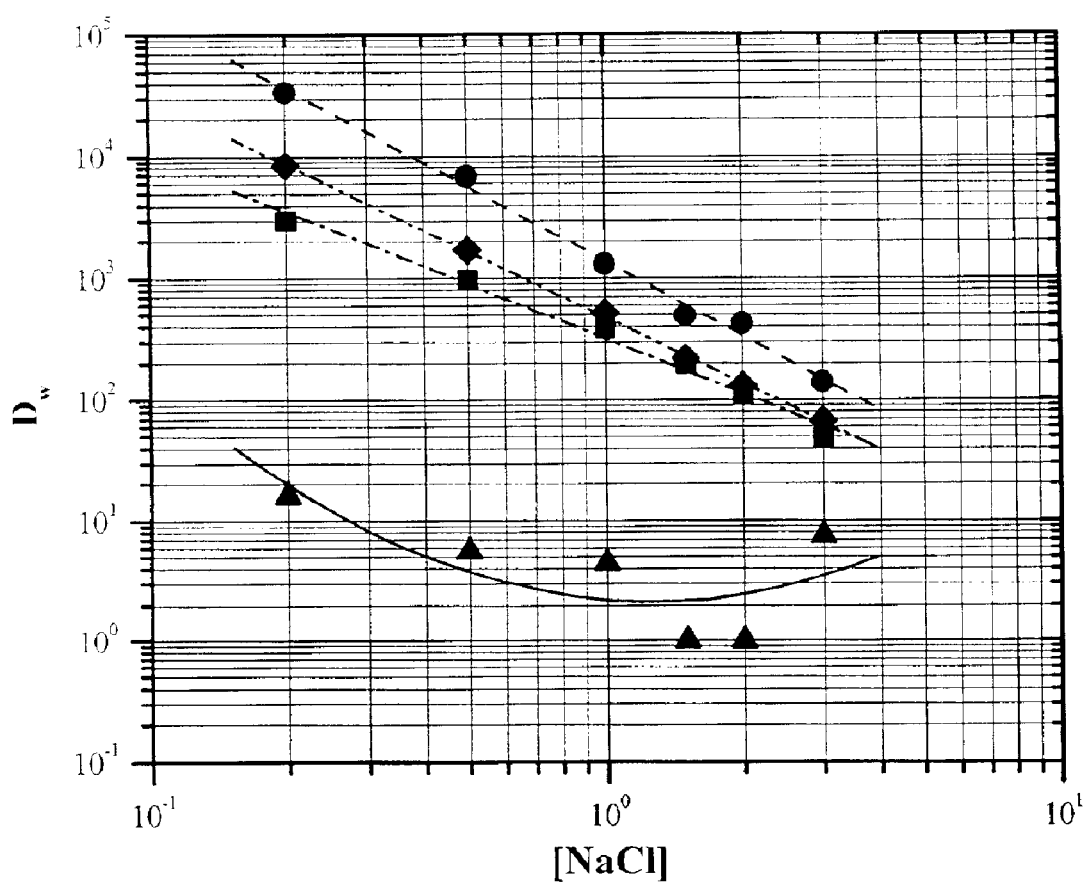
FIG. 12 is a graph of $D_w$ values for Ra(II) (closed squares), Ba(II) (closed diamonds), Ce(III) (closed circles), and Bi(III) (closed triangles) vs. [NaCl] in 0.50 M (Na,H) OAc buffer at pH=4.0 on a Bio-Rad® AGMP-50 cation-exchange resin.

Considering the medical application, somewhat higher DF values are desired and can be obtained by using the Bio-Rad® AGMP-50 macroporous sulfonic acid cation-exchange resins, as shown in FIG. 12. Decontamination factors of Bi(III) from Ra(II) and Ce(III) in about 0.75 M NaCl in 0.50 M (Na,H)OAc at pH=4.0 obtained using the AGMP-50 cation-exchange resin are about 130 and about 640, respectively. Although the DF values for Ra(II) exhibited by the 50W×8 and AGMP-50 cation-exchange resins are comparable at 110 and 130, respectively, the DF values for Ce(III) [and by extension Ac(III)] are over twice as large for the AGMP-50 resin as compared to the 50W×8 resin(i.e., 250 vs. 640).

Figure 13:
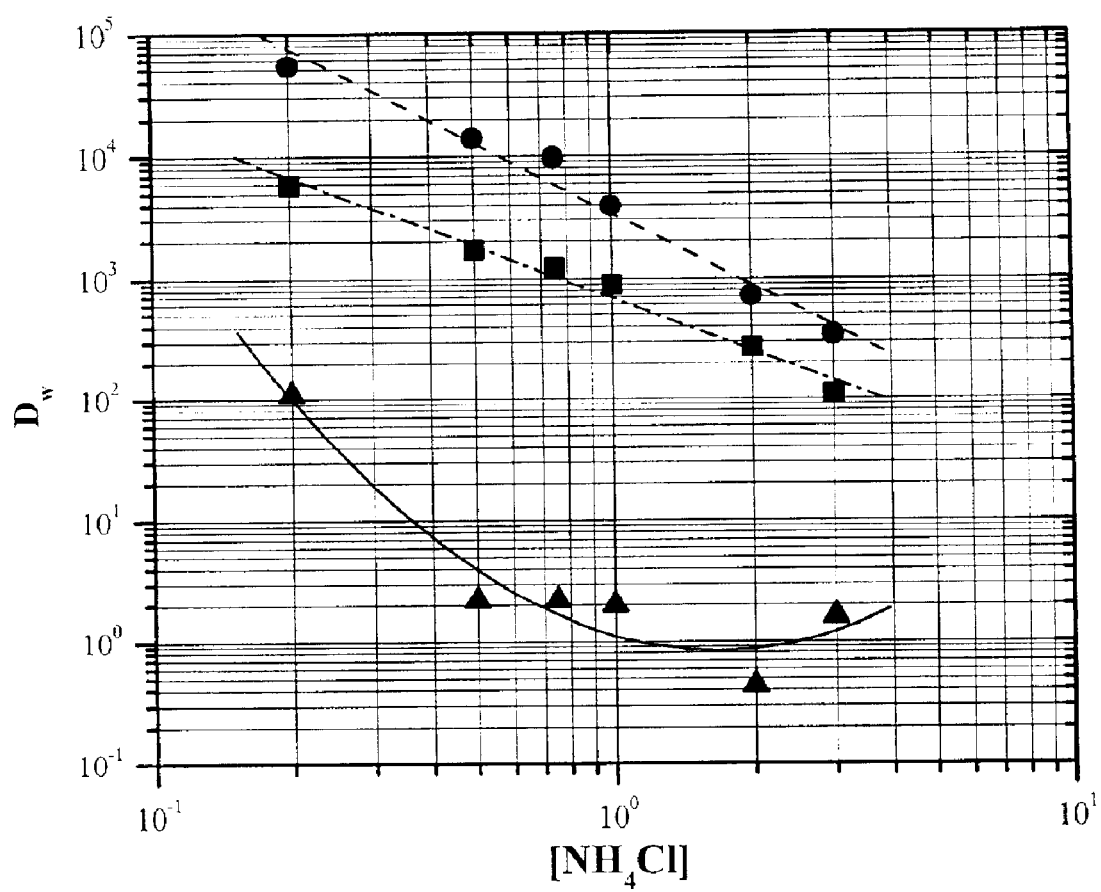
FIG. 13 is a graph of $D_w$ values for Ra(II) (closed squares), Ce(III) (closed circles), and Bi(III) (closed triangles) vs. [NH$_4$Cl] in 0.50 M ammonium acetate [(NH$_4$, H)OAc] buffer at pH=4.0 on a Bio-Rad® AGMP-50 cation exchange resin.

An ammonium acetate $[(NH_4,H)OAc]$ buffer solution can be used in place of (Na,H)OAc buffer, and FIG. 13 shows that $D_w$ values for Ra(II) and Ce(III) are somewhat higher than the values obtained for the same resin in a $Na^{1+}$ system. Calculated DF values for Bi(III) from Ra(II) and Ce(III) of about 710 and about 5700, respectively, are attainable from 0.75 M $NH_4Cl$ in 0.50 M $(NH_4,H)OAc$ at pH=4.0. However promising are the elevated DFs attainable in the $NH_4^{1+}$ system, the intravenous administration of most medications occurs in appropriately buffered NaCl solutions, which strongly favors the use of NaCl and the (Na,H)OAc buffer.

The performance data discussed above coupled with the observations made earlier that $^{225}$Ac is the optimal generator source material, collectively support the use of AGMP-50 or similar cation-exchange resin in the guard column. Overall, the potential for producing a highly pure $^{213}$Bi product in a NaCl/(Na,H)OAc buffer solution at pH=4.0 is appealing as pharmaceutical grade NaCl, HOAc, and NaOH are all commercially available. Further, (Na,H)OAc buffer solutions and NaCl solutions are routinely used in radioconjugation reactions in nuclear medicine.

EXAMPLE 4

Multicolumn Selectivity Inversion Generator

Figure 14:
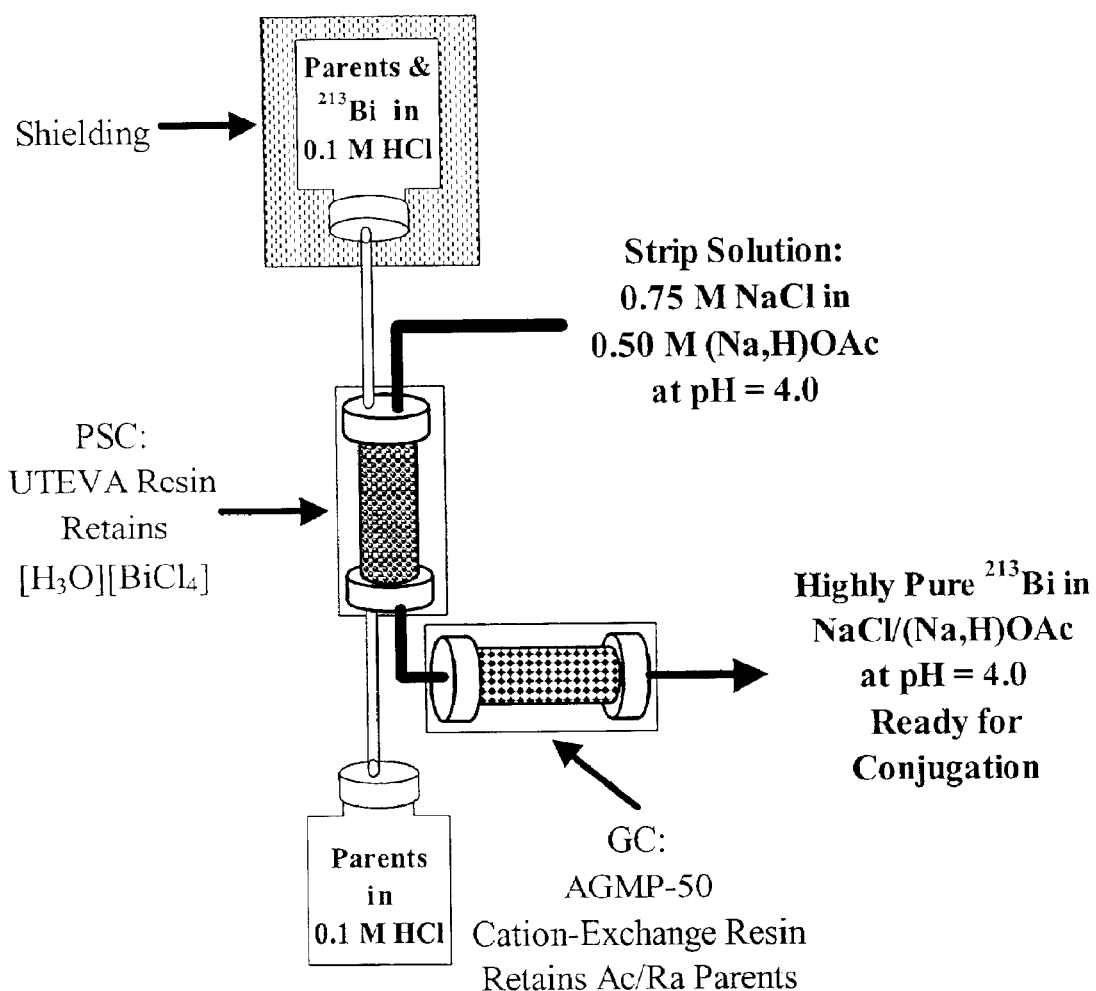
FIG. 14 is a schematic representation of a set of optimal conditions for the purification of $^{213}$Bi by a multicolumn selectivity inversion generator.

Based on the results of FIGS. 6–13, conditions for the production of $^{213}$Bi(III) using a multicolumn selectivity inversion generator have been established and are presented in FIG. 14. Initially, the $^{225}$Ac(III) source material is permitted to approach radioactive steady state with its daughters in 0.10 M HCl. When needed, the $^{213}$Bi(III) is extracted from the radionuclide mixture by binding to a UTEVA® Resin primary separation column that retains [H$_3$O][BiCl$_4$]. The UTEVA® Resin eluate, depleted of $^{213}$Bi(III), is collected and again permitted to approach radioactive steady state for future use.

After rinsing with 3 BV of pristine 0.10 M HCl to remove interstitial radionuclidic and chemical impurities, the $^{213}$Bi(III) is stripped (eluted) from the primary separation column using 0.75 M NaCl in 0.50 M (Na,H)OAc at pH=4.0. This eluate from the primary separation column is directed without chemical adjustment through the AGMP-50 macroporous sulfonic acid cation-exchange resin guard column. This guard column retains any potential long-lived $^{225/224}$Ra(II) or $^{225}$Ac(III) contaminants to ensure the high radionuclidic purity of the $^{213}$Bi(III) product.

Additional $^{213}$Bi can be recovered from astatinic acid (HAt) and/or heteroleptic monoanionic Cl$^-$/At$^-$ complexes of Bi(III) that could theoretically be retained by UTEVA® Resin, although the "hot atom" chemistry of the latter probably leads to an unstable complex. Bismuth-213 arising from the rapid decay of $^{221}$Fr could be recovered by performing a second separation on the primary separation column about 17 minutes after the initial processing run.

EXAMPLE 5

LSC and γ Spectral Studies

Given that the previously-described process optimization studies relied on the chemical similarities between Ce(III) and Ac(III), several detailed studies using $^{225}$Ac(III) were undertaken to confirm the selection of the separation media and solution conditions, and to determine the overall DF values attainable by this multicolumn selectivity inversion generator. Initial studies with $^{225}$Ac(III) used the chemical parameters defined in FIG. 14 and searched for differences in the LSC and γ spectra of different samples collected during processing.

The 0–2000 keV LSC (i.e., α and β$^{1-}$) and 0–1000 keV γ spectra for five different samples were taken during the purification of $^{213}$Bi(III) using the conditions specified in FIG. 14. The initial LSC spectrum for $^{225}$Ac in 0.10 M HCl at radioactive steady state with its daughters showed a broad peak centered at about 500 keV with a shoulder at about 600 keV. The initial γ spectrum shows three major peaks at less than 100 keV, 218 keV, and 440 keV.

The spectra obtained for the eluate from the UTEVA® Resin primary separation column, which is depleted of $^{213}$Bi (except for ingrowth) showed some qualitative differences in both the LSC and γ spectra, with the LSC spectrum becoming somewhat more detailed and the peak at about 600 keV becoming less prominent. The γ spectrum exhibits a change in the relative peak heights as compared to the initial values.

Spectra for the strip of the UTEVA® Resin primary separation column showed that substantial differences in the spectra emerge. The LSC spectrum showed a significant decrease in intensity of the peaks centered around about 500 keV, and somewhat more detail appears in the form of low and high energy shoulders around the about 600 keV peak. The most dramatic difference in the γ spectral fingerprint was the disappearance of the 218 keV peak and increased intensity of the 440 keV peak relative to the peak at less than 100 keV.

Spectral results for the eluate from the AGMP-50 cation-exchange resin guard column very closely resembled the spectra from the strip of the primary separation column, which most likely represents radionuclidically pure $^{213}$Bi.

Spectral results were obtained for an experimental 6.0 M HCl strip of the AGMP-50 cation-exchange resin guard column. The γ spectrum suggested that a very small amount of $^{213}$Bi(III) is retained by the guard column and, combined with the branching decay and 3.25 hour half-life $^{209}$Pb, are responsible for the low energy LSC spectrum.

The γ spectra depict the most useful diagnostic probes of the separation efficiency, with the column strip solution and guard column eluate showing only two peaks. An examination of the reported γ-emissions [see, Lederer et al., Eds. *Table of Isotopes;* 7th ed.; John Wiley and Sons: New York, 1978] for each of the $^{225}$Ac decay products shows that the peak at 218 keV corresponds to $^{221}$Fr and the 440 keV peak is attributable to $^{213}$Bi. The low energy peaks at less than 100 keV were not well resolved with the instrumentation used in these studies, and these peaks were not used as diagnostic probes. Because of the short half-life of $^{221}$Fr (4.8 minutes, FIG. 2), this radionuclide quickly achieves radioactive steady state with its $^{225}$Ac parent and can thus be employed as an indirect probe of $^{225}$Ac behavior.

EXAMPLE 6

Worst-case Scenario Challenges

Two chromatographic separations of $^{213}$Bi(III) from $^{225}$Ac(III) were performed as "worst case scenario" challenges to the multicolumn selectivity inversion generator. This objective was accomplished by independently contacting solutions of $^{225}$Ac(III) at radioactive steady state with its daughters with either the UTEVA® Resin primary separation column or the AGMP-50 cation-exchange resin guard column (i.e., the two columns were not used in tandem as shown in FIG. 14). By examining the $^{225}$Ac(III) and $^{213}$Bi(III) elution profiles of each column operating independently and monitoring the decay of a $^{213}$Bi sample taken from each, independent decontamination factors for each stage of the process can be determined.

Figure 15:
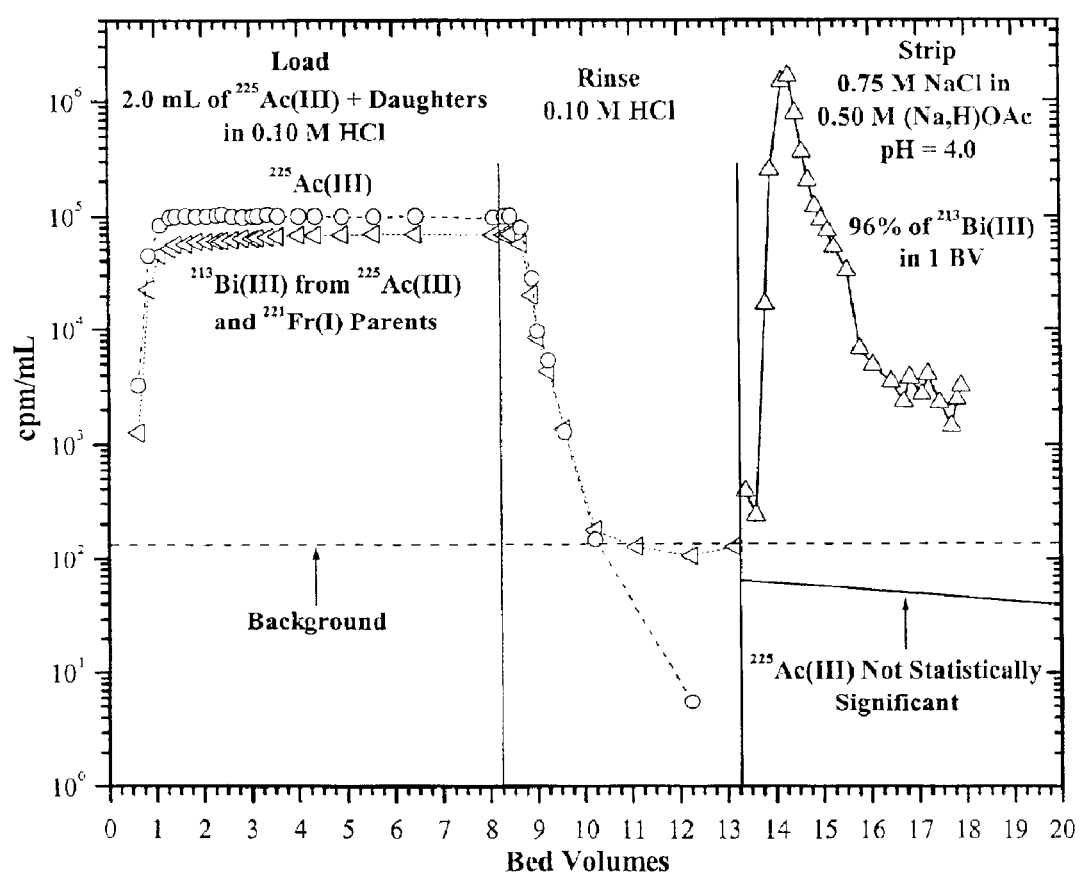
FIG. 15 is a graph of cpm/mL vs. bed volumes of eluate for the purification of $^{213}$Bi (open triangles) from a solution also containing $^{225}$Ac(III) (open circles) by a 0.25 mL UTEVA® Resin primary separation column loaded and rinsed with 0.10 M HCl, and stripped with a solution of 0.75 M NaCl in 0.50 M (Na,H)OAc at pH=4.0 and 25(±2)° C.

FIG. 15 shows the chromatographic separation of $^{213}$Bi(III) from its $^{225}$Ac(III) parent in 0.10 M HCl by UTEVA® Resin at 25(±2)° C. Actinium-225, monitored here using the $^{221}$Fr γ-emission, elutes with the first free column volume of the 0.10 M HCl load solution and reaches background radiation levels after only 2 BV of rinse with pristine 0.10 M HCl. Bismuth-213 is detected in these load samples and is an artifact of the rapid radioactive ingrowth from the $^{221}$Fr parent that is present in the eluate from the UTEVA® Resin primary separation column. Stripping with 0.75 M NaCl in 0.50 M sodium acetate [(Na,H)OAc] buffer at pH=4.0 removes 96 percent of the $^{213}$Bi(III) in 1 BV, and no statistically significant $^{225}$Ac(III) (or $^{221}$Fr(I)) could be detected in the strip samples. The sharp elution band indicates efficient stripping and is advantageous in that small solution volumes permit the production of high specific activity samples that can be conveniently diluted as needed. FIG. 15 also shows that a DF value for $^{213}$Bi(III) from $^{225}$Ac(III) and $^{221}$Fr(I) of more than $10^4$ is achieved using only the UTEVA® Resin primary separation column.

Figure 16:
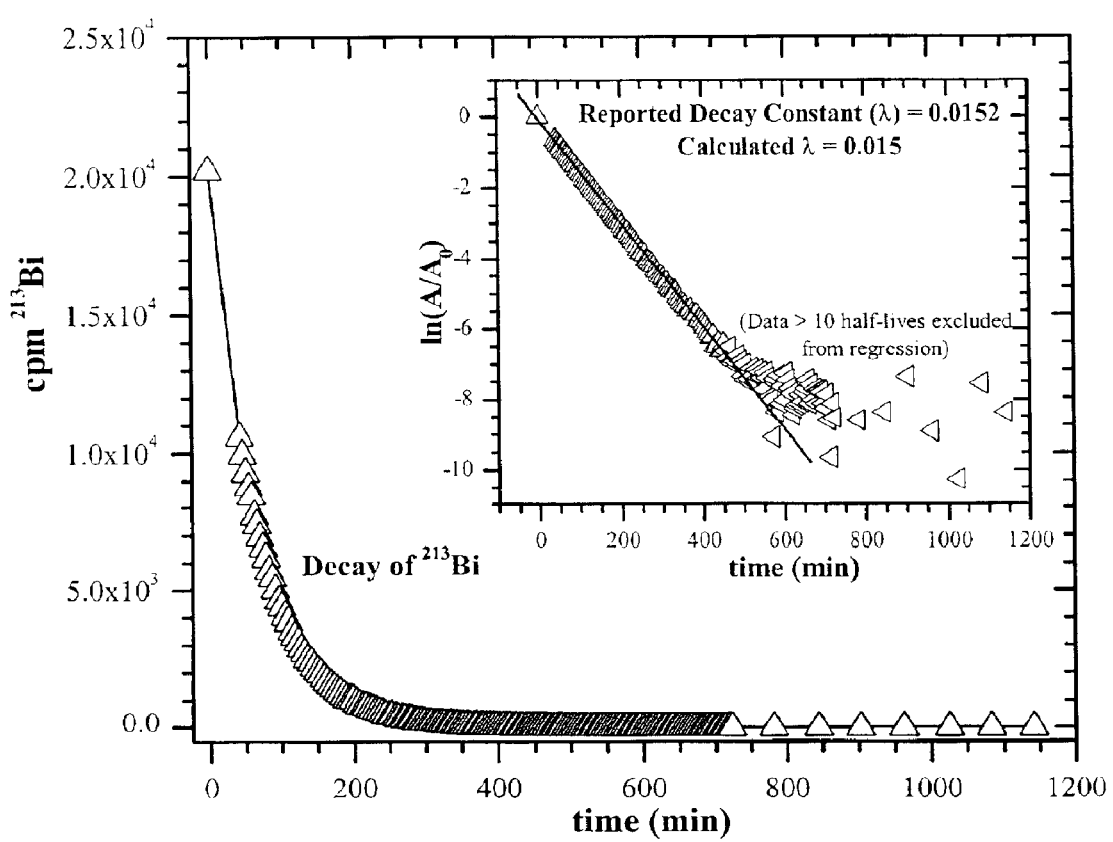
FIG. 16 is a graph of cpm vs. time for the decay of a $^{213}$Bi(III) sample obtained at the stripping peak maximum shown in FIG. 15 after loading $^{225}$Ac(III) and daughter radionuclides in 0.10 M HCl, rinsing with 0.10 M HCl, and stripping with 0.75 M NaCl in 0.50 M (Na,H)OAc at pH=4.0 using gravity flow at 25(±2)° C. The insert graph is a plot of $\ln(A/A_0)$ vs. time and shows the linear relationship between the reported decay constant (line) and the experimental data.

As a test of the radionuclidic purity of the $^{213}$Bi(III) separated using the UTEVA® Resin, the radioactive decay of a sample taken at the stripping peak maximum (i.e., the sample with the highest count rate in the stripping region of FIG. 15) was continuously measured for about 20 hours. FIG. 16 shows the results of the $^{213}$Bi decay curve, which reaches background radiation levels after ten half-lives (i.e., about 450 minutes).

The inset plot shows in $(A/A_0)$ vs. time, which is linear through the first ten half-lives of $^{213}$Bi after which a plateau is observed as the count rate approaches background radiation levels and instrumental limitations. The reported decay constant ($\lambda$) for $^{213}$Bi is $\lambda$=0.0152 min$^{-1}$ [see, Lederer et al., Eds. *Table of Isotopes;* 7th ed.; John Wiley and Sons: New York, 1978], and the experimentally calculated $\lambda_{calc}$=0.015 min$^{-1}$ indicates that the $^{213}$Bi is of quite high radionuclidic purity (and also supports the assignment of the 440 keV γ peak to $^{213}$Bi)

These data suggest that the UTEVA® Resin primary separation column alone provides $^{213}$Bi of high radionuclidic purity; however, the slight tail in the plot of in $(A/A_0)$ vs. time in FIG. 16 cannot be conclusively attributed to instrumental limitations and could result from a very trace amount of $^{225}$Ac impurity. As a result, the guard column chemistry is highly recommended as adventitious trace radionuclidic impurities are scavenged to ensure that no long-lived radionuclidic parents exit the generator system.

Figure 17:
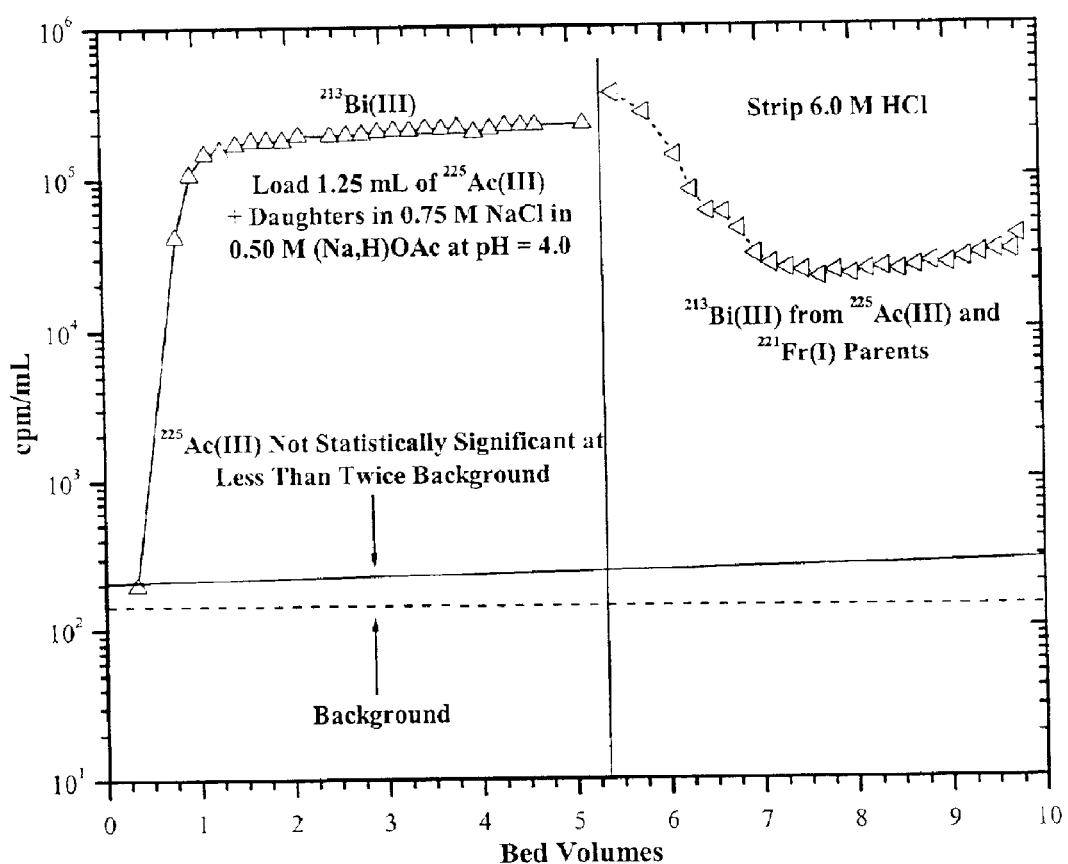
FIG. 17 is a graph of cpm/mL vs. bed volumes of eluate for the purification of a $^{213}$Bi(III) sample taken at about 3.5 BV on a 0.25 mL bed of Bio-Rad® AGMP-50 cation-exchange resin guard column preequilibrated with 0.75 M NaCl in 0.50 M (Na,H)OAc at pH=4.0, loaded with $^{225}$Ac (III) and daughter radionuclides in 0.75 M NaCl in 0.50 M (Na,H)OAc at pH=4.0, and stripped with 6.0 M HCl at 25(±2)° C.

FIG. 17 shows a rigorous test of the AGMP-50 cation-exchange resin guard column, which was contacted with a mixture of $^{225}$Ac(III) and its daughters at radioactive steady state. Such a mixture would only encounter the guard column in the event of a catastrophic failure of the primary separation column, and thus represents a worst-case challenge of the guard column. As shown, the 0.75 M NaCl in 0.50 M (Na,H)OAc solution at pH=4.0 causes immediate elution of $^{213}$Bi(III) with no statistically significant breakthrough of $^{225}$Ac(III) or $^{221}$Fr(I).

An experimental strip with 6.0 M HCl removes some $^{213}$Bi(III), most likely from decay by the cationic $^{225}$Ac(III) and $^{221}$Fr(I) parents that are retained by the AGMP-50 cation-exchange resin. One notable aspect of the 6.0 M HCl strip study is the absence of a significant spike in count rate upon crossover to 6.0 M HCl, which indicates that no significant quantities of $^{213}$Bi(III) are retained by the AGMP-50 cation-exchange resin guard column. operating independently and encountering greater than $10^4$ times more $^{225}$Ac(III) than expected, the AGMP-50 cation-exchange resin guard column yielded a DF value of $^{213}$Bi(III) from $^{225}$Ac(III) and $^{221}$Fr(I) of at least $10^3$.

Figure 18:
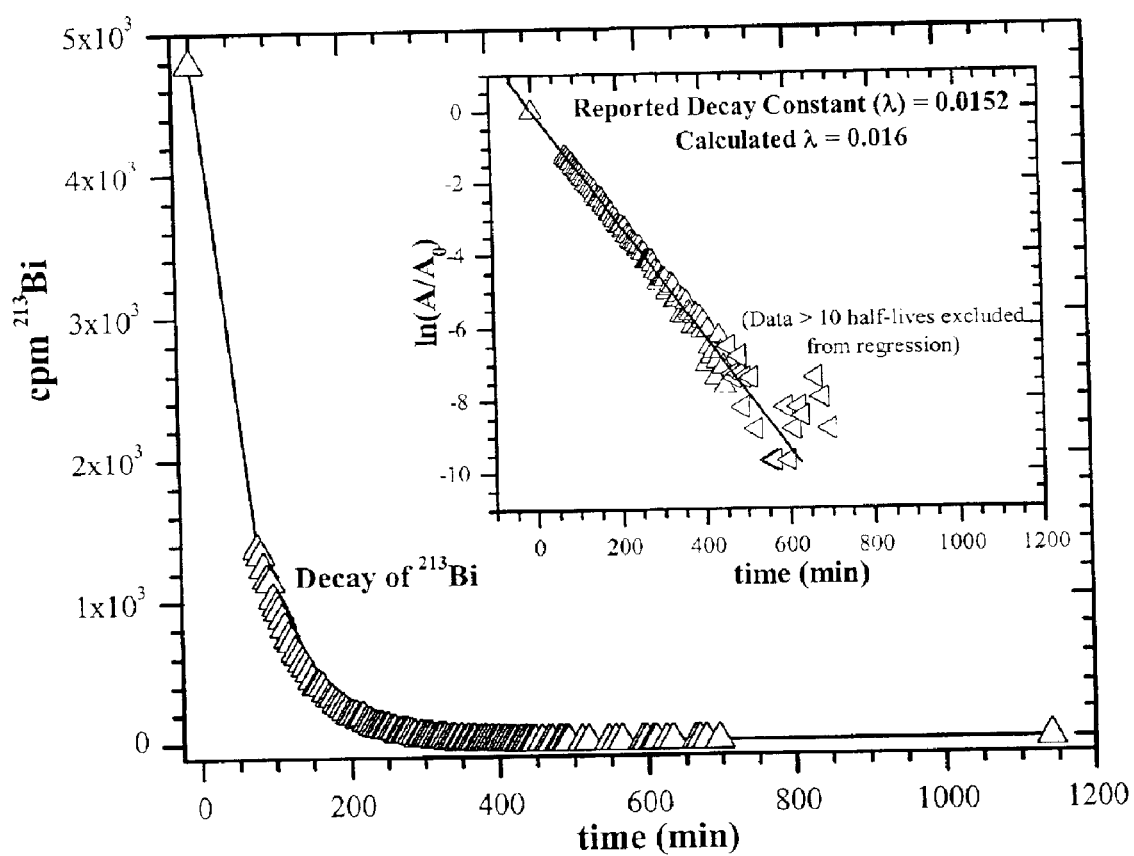
FIG. 18 is a graph of cpm vs. time for the decay of a $^{213}$Bi(III) sample obtained at about 3.5 BV shown in FIG. 17 after loading with $^{225}$Ac(III) and daughter radionuclides in 0.75 M NaCl in 0.50 M (Na,H)OAc at pH=4.0 and stripped with 6.0 M HCl at $^{25}$(±2)° C. The insert graph is a plot of $\ln(A/A_0)$ vs. time and shows the linear relationship between the reported decay constant (line) and the experimental data.

The radionuclidic purity of a $^{213}$Bi sample taken toward the end of the loading plateau of FIG. 17 was monitored for radioactive decay in a manner similar to that of FIG. 16. The decay curve of this $^{213}$Bi sample is shown in FIG. 18, and again the $^{213}$Bi activity decreases regularly to background radiation levels over ten half-lives. The inset shows linear decay with $\lambda_{calc}$=0.016, indicating a $^{213}$Bi sample of high radionuclidic purity.

The data of FIGS. 13–16 show that the UTEVA® Resin primary separation column and the AGMP-50 cation-exchange resin guard column can independently yield DF values of $^{213}$Bi(III) from $^{225}$Ac(III) and $^{221}$Fr(I) of at least $10^4$ and $10^3$, respectively. The combination of these two separation media into a single multicolumn selectivity inversion generator magnifies the overall DF to about $10^6$ or $10^7$, and virtually ensures the production of $^{213}$Bi of high chemical and radionuclidic purity.

EXAMPLE 7

MilliCurie Level Scale-up of Separations

Figure 19:
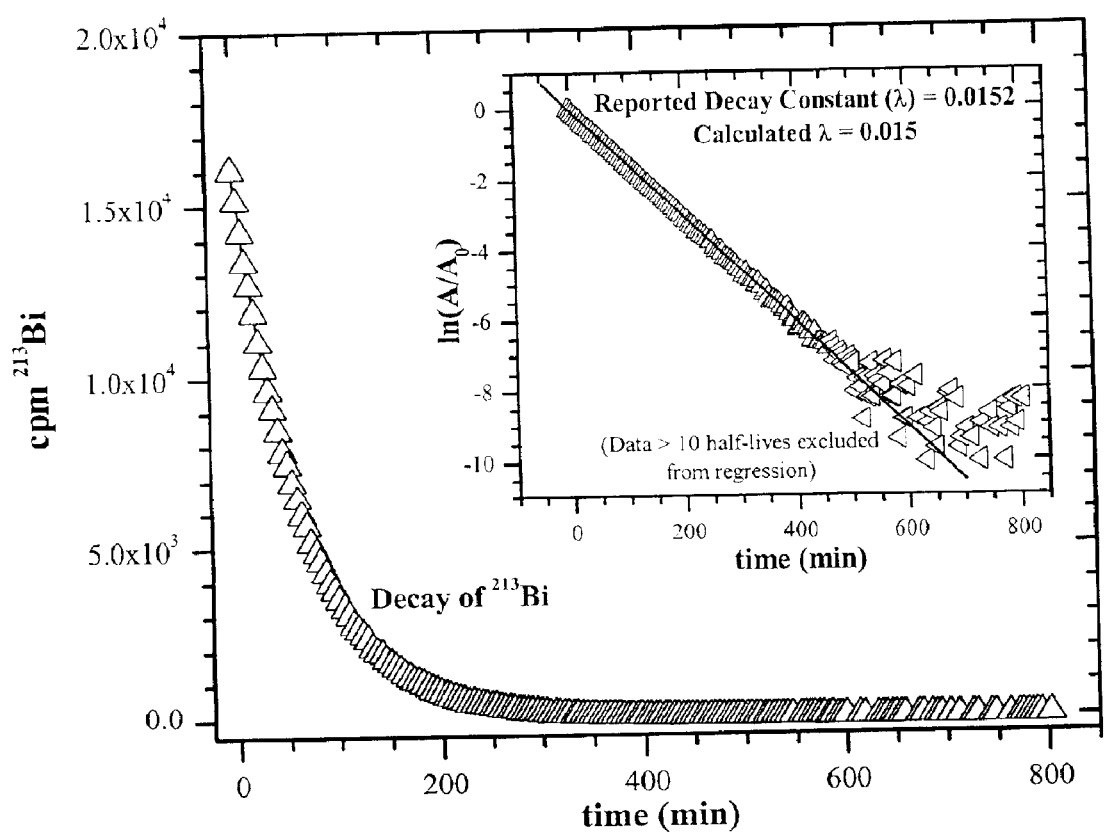
FIG. 19 is a plot of cpm vs. time for the decay of $^{213}$Bi purified from about 5 mCi of $^{225}$Ac(III) and daughter radionuclides in 0.10 M HCl on UTEVA® Resin, rinsed with 0.10 M HCl, stripped with 0.75 M NaCl in 0.50 M (Na,H)OAc at pH=4, and eluted through a BioRad® AGMP-50 cation-exchange resin using gravity flow at 25(±2)° C. The insert graph is a plot of $\ln(A/A_0)$ vs. time and shows the linear relationship between the reported decay constant (line) and the experimental data.

Because all previous studies were performed using $\mu$Ci levels of $^{225}$Ac on pristine (not previously used) chromatographic columns, a series of 500-fold scale-up experiments were performed using about 5 mCi of $^{225}$Ac. FIG. 19 shows the decay curve and linear decrease in $^{213}$Bi activity through ten half-lives for a $^{213}$Bi sample purified from about 5 mCi of $^{225}$Ac using the multicolumn selectivity inversion generator described in FIG. 14. These columns had been used at least once before in the purification of about 5 mCi of $^{213}$Bi and did not show any substantial differences in separation efficiency or chromatographic behavior. The exceptional agreement between the reported $\lambda$=0.0152 min$^{-1}$ and $\lambda_{calc}$= 0.015 min$^{31\ 1}$ is indicative of the high radionuclidic purity of $^{213}$Bi. A conservatively estimated DF of $^{213}$Bi(III) from $^{225}$Ac(III) of more than $10^7$ has been calculated for this purification of about 5 mCi of $^{213}$Bi by the multicolumn selectivity inversion generator shown in FIG. 14.

EXAMPLE 8

Radiation Sterilization Studies

Additional studies have been performed to examine the effects of radiation sterilization of the chromatographic materials. Radiation sterilization at a dose of 25 kGy of the UTEVA® Resin primary separation column for the separation of $^{213}$Bi(III) from $^{225}$Ac(III) shows statistically identical behavior between raw (i.e., not sterilized) UTEVA® Resin and that sterilized with 25 kGy of radiation (investigated using $^{139}$Ce(III) and $^{207}$Bi(III)). The immediate breakthrough of AC(III) [Ce(III)] during loading, the decrease to background after two bed volumes of rinse, and the very narrow stripping bands yielding virtually all of the Bi(III) activity in one bed volume are strong indicators that the radiation sterilization of UTEVA® Resin does not alter its performance in the separation of $^{213}$Bi(III) from $^{225}$Ac(III) and its radiogenic daughters.

A similar study of nonsterile and sterilized resins was undertaken for the AGMP-50 cation-exchange resin guard column. Again, similar behavior in the breakthrough of the Bi(III) and the absence of statistically significant quantities of Ac(III) or Ce(III) in the eluate suggests that the sterilized AGMP-50 cation-exchange resin guard columns effectively sorb $^{225}$Ac(III) contaminants while permitting $^{213}$Bi(III) to elute.

Each of the patents, patent applications and articles cited herein is incorporated by reference. The use of the article "a" or "an" is intended to include one or more.

From the foregoing it will be observed that numerous modifications and variations can be effectuated without departing from the true spirit and scope of the novel concepts of the invention. It is to be understood that no limitation with respect to the specific embodiment illustrated is intended or should be inferred. The disclosure is intended to cover by the appended claims all such modifications as fall within the scope of the claims.

What is claimed:

1. A method for producing a solution of trivalent bismuth-213 daughter radionuclide ions that is substantially free of divalent radium-225 and trivalent actinium-225 parent and other daughter radionuclide ion impurities comprising the steps of:

(a) contacting an aqueous acidic parent-daughter radionuclide ion solution containing trivalent bismuth-213 daughter radionuclide ions with a separation medium having a high affinity for the bismuth-213 daughter radionuclide and a low affinity for the parent and other daughter radionuclides, said separation medium comprising a phosphorus-containing extractant having a phosphoryl bond and the remaining bonds from phosphorus are to one or more of (i) a carbon atom of a $C_1$–$C_{10}$ alkyl group, a benzyl group, a carboxamido $C_1$–$C_6$ alkyl group whose amido nitrogen atom has the formula —$NR^1R^2$ and a phenyl group, (ii) a polymer backbone, (iii) an O—$R^1$ group wherein $R^1$ is a hydrido group, a $C_1$–$C_{10}$ alkyl group, a phenyl group or a benzyl group, (iv) a —$NR^1R^2$ group, and (v) a divalent radical selected from the group consisting of an imino group, a $C_1$–$C_{10}$ cyclic or acyclic hydrocarbylene group, a phenylene group and a xylylene group, where each of the $R^1$ and $R^2$ groups is the same or different and is as defined for $R^1$, and maintaining that contact for a time period sufficient for said bismuth-213 ions to be bound by the separation medium to form bismuth-213-laden separation medium and a daughter-depleted parent-daughter solution;

(b) removing the daughter-depleted parent-daughter solution from the separation medium; and (c) stripping the daughter radionuclide from the daughter-laden separation medium with an aqueous solution to form an aqueous solution of trivalent bismuth-213 daughter radionuclide ions that is substantially free of divalent radium-225 and trivalent actinium-225 parent and other daughter radionuclide ion impurities.

2. The method according to claim 1 wherein the decontamination factor of the bismuth-213 daughter from the parent radionuclide impurities of the separation medium under the conditions of contact is about $10^1$ or greater.

3. The method according to claim 1 wherein said separation medium is particulate.

4. The method according to claim 3 wherein said separation medium is comprised of a water-insoluble phosphorus-containing extractant having a phosphoryl bond that is coated on particles.

5. A method for producing a solution of trivalent bismuth-213 daughter radionuclide ions that is substantially free of divalent radium-225 and trivalent actinium-225 parent and other daughter radionuclide ion impurities comprising the steps of:

(a) contacting an aqueous acidic parent-daughter radionuclide ion solution containing bismuth-213 daughter radionuclide ions with a separation medium that provides a decontamination factor of the bismuth-213 daughter ions from the parent and other daughter radionuclide ion impurities under the conditions of contact of about $10^1$ or greater, said separation medium comprising a water-insoluble phosphorus-containing extractant having a phosphoryl bond coated on particles wherein the remaining bonds from phosphorus are to one or more of (i) a carbon atom of a $C_1$–$C_{10}$ alkyl group, a benzyl group, a carboxamido $C_1$–$C_6$ alkyl group whose amido nitrogen atom has the formula —$NR^1R^2$ and a phenyl group, (ii) an O—$R^1$ group wherein $R^1$ is a hydrido group, a $C_1$–$C_{10}$ alkyl group, a phenyl group or a benzyl group, (iii) a —$NR^1R^2$ group and (iv) a divalent radical selected from the group consisting of an imino group, a $C_1$–$C_{10}$ cyclic or acyclic hydrocarbylene group, a phenylene group and a xylylene group, where each of the $R^1$ and $R^2$ groups is the same or different and is as defined for $R^1$, and maintaining that contact for a time period sufficient for said bismuth-213 ions to be bound by the first separation medium to form bismuth-213-laden separation medium and a daughter-depleted parent-daughter solution;

(b) removing the daughter-depleted parent daughter solution from the separation medium; and (c) stripping the daughter radionuclide from the daughter-laden separation medium with an aqueous solution to form an aqueous solution of bismuth-213 ions to form an aqueous solution of trivalent bismuth-213 daughter radionuclide ions that is substantially free of divalent radium-225 and trivalent actinium-225 parent and other daughter radionuclide ion impurities.

6. The method according to claim 5 wherein the decontamination factor between bismuth-213 daughter radionuclide and divalent radium-225 and trivalent actinium-225 parent and other daughter radionuclide ion impurities of said separation medium under the conditions of contact is about $10^2$ or more.

7. The method according to claim 5 wherein said aqueous acidic parent-daughter radionuclide ion solution containing bismuth-213 daughter radionuclide ions contains hydrochloric acid at a concentration of about 0.02 to about 0.4 M.

8. The method according to claim 5 wherein said water-insoluble phosphorus-containing extractant is a phosphine oxide, phosphinate, phosphonate, or phosphate.

9. The method according to claim 5 wherein the aqueous stripping solution of step (c) is a salt solution buffered at a pH value of about 3 to about 7.

10. The method according to claim 5 including the further step of recovering said solution of trivalent bismuth-213 daughter radionuclide that is substantially free of divalent radium-225 and trivalent actinium-225 parental radionuclide ion impurities.

11. A method for producing a solution of trivalent bismuth-213 daughter radionuclide ions that is substantially free of divalent radium-225 and trivalent actinium-225 parent and other daughter radionuclide ion impurities comprising the steps of:

(a) contacting an aqueous acidic parent-daughter radionuclide ion solution containing bismuth-213 daughter radionuclide ions with a first separation medium having a high affinity for the bismuth-213 daughter radionuclide and a low affinity for the parent and other daughter radionuclides, said first separation medium comprising a phosphorus-containing extractant having a phosphoryl bond and the remaining bonds from phosphorus are to one or more of (i) a carbon atom of a $C_1$–$C_{10}$ alkyl group, a benzyl group, a carboxamido $C_1$–$C_6$ alkyl group whose amido nitrogen atom has the formula —$NR^1R^2$ and a phenyl group, (ii) a polymer backbone, (iii) an O—$R^1$ group wherein $R^1$ is a hydrido group, a $C_1$–$C_{10}$ alkyl group, a phenyl group or a benzyl group, (iv) a —$NR^1R^2$ group and (v) a divalent radical selected from the group consisting of an imino group, a $C_1$–$C_{10}$ cyclic or acyclic hydrocarbylene group, a phenylene group and a xylylene group, where each of the $R^1$ and $R^2$ groups is the same or different and is as defined for $R^1$, and maintaining that contact for a time period sufficient for said bismuth-213 ions to be bound by the first separation medium to form bismuth-213-laden separation medium and a daughter-depleted parent-daughter solution;

(b) removing the daughter-depleted parent-daughter solution from the separation medium;

(c) stripping the daughter radionuclide from the daughter-laden separation medium with an aqueous solution to form an aqueous solution of bismuth-213 ions; and (d) contacting the aqueous solution of bismuth-213 ions with a second separation medium that is a polymeric cation-exchange resin having a high affinity for the parent radionuclide ions and a low affinity for said bismuth-213 daughter radionuclide ions, and maintaining that contact for a time period sufficient for said parent radionuclide to be bound by the second separation medium to form a solution of trivalent bismuth-213 daughter radionuclide that is substantially free of divalent radium-225 and trivalent actinium-225 parent and other daughter radionuclide ion impurities.

12. The method according to claim 11 wherein the combined decontamination factor of the bismuth-213 daughter from the parent radionuclide impurities of both the first and second separation media under the conditions of contact is about $10^4$ or greater.

13. The method according to claim 11 wherein said first separation medium is particulate.

14. The method according to claim 13 wherein said first separation medium is comprised of a water-insoluble phosphorus-containing extractant having a phosphoryl bond that is coated on particles.

15. The method according to claim 11 wherein said second separation medium is a particulate polymer.

16. A method for producing a solution of trivalent bismuth-213 daughter radionuclide ions that is substantially free of divalent radium-225 and trivalent actinium-225 parent and other daughter radionuclide ion impurities comprising the steps of:

(a) contacting an aqueous acidic parent-daughter radionuclide ion solution containing bismuth-213 daughter radionuclide ions with a first separation medium having a high affinity for the bismuth-213 daughter radionuclide and a low affinity for the parent and other daughter radionuclides, said first separation medium comprising a water-insoluble phosphorus-containing extractant having a phosphoryl bond coated on particles wherein the remaining bonds from phosphorus are to one or more of (i) a carbon atom of a $C_1$–$C_{10}$ alkyl group, a benzyl group, a carboxamido $C_1$–$C_6$ alkyl group whose amido nitrogen atom has the formula —$NR^1R^2$ and a phenyl group, (ii) an O—$R^1$ group wherein $R^1$ is a hydrido group, a $C_1$–$C_{10}$ alkyl group, a phenyl group or a benzyl group, (iii) a —$NR^1R^2$ group and (iv) a divalent radical selected from the group consisting of an imino group, a $C_1$–$C_{10}$ cyclic or acyclic hydrocarbylene group, a phenylene group and a xylylene group, where each of the $R^1$ and $R^2$ groups is the same or different and is as defined for $R^1$, and maintaining that contact for a time period sufficient for said bismuth-213 ions to be bound by the first separation medium to form bismuth-213-laden separation medium and a daughter-depleted parent-daughter solution;

(b) removing the daughter-depleted parent daughter solution from the separation medium;

(c) stripping the daughter radionuclide from the daughter-laden separation medium with an aqueous solution to form an aqueous solution of bismuth-213 ions;

(d) contacting the aqueous solution of bismuth-213 ions with a second separation medium that is a particulate polymeric cation-exchange resin having a high affinity for the parent radionuclide ions and a low affinity for said daughter radionuclide ions, wherein the combined decontamination factor of the bismuth-213 desired daughter from the parent radionuclide impurities of both the first and second separation media under the conditions of contact is about $10^4$ or greater, and maintaining that contact for a time period sufficient for said parent radionuclide to be bound by the second separation medium to form a solution of trivalent bismuth-213 daughter radionuclide that is substantially free of divalent radium-225 and trivalent actinium-225 parent radionuclide ion impurities.

17. The method according to claim 16 wherein the decontamination factor of the bismuth-213 daughter from the parent radionuclide impurities of said first separation medium under the conditions of contact is about $10^2$ or more.

18. The method according to claim 16 wherein the decontamination factor between radioactive parent and bismuth-213 daughter radionuclide of said second separation medium under the conditions of contact is about $10^2$ or more.

19. The method according to claim 16 wherein said aqueous acidic parent-daughter radionuclide ion solution containing bismuth-213 daughter radionuclide ions contains hydrochloric acid at a concentration of about 0.02 to about 0.4 M.

20. The method according to claim 16 wherein said water-insoluble phosphorus-containing extractant is a phosphine oxide, phosphinate, phosphonate, or phosphate.

21. The method according to claim 16 wherein the aqueous stripping solution of step (c) is a salt solution buffered at a pH value of about 3 to about 7.

22. The method according to claim 16 wherein said second separation medium that is a particulate polymeric cation-exchange resin is a particulate sulfonic acid polymeric cation-exchange resin.

23. A method for producing a solution of trivalent bismuth-213 daughter radionuclide ions that is substantially free of divalent radium-225 and trivalent actinium-225 parent radionuclide ion impurities comprising the steps of:

(a) contacting an aqueous acidic parent-daughter radionuclide ion solution containing hydrochloric acid at a concentration of about 0.02 to about 0.4 M and bismuth-213 daughter radionuclide ions with a first separation medium that provides a decontamination factor of the bismuth-213 daughter from the parent radionuclide impurities under the conditions of contact is about $10^2$ or more, said first separation medium comprising a water-insoluble phosphorus-containing extractant having a phosphoryl bond coated on particles that is a phosphine oxide or phosphonate in which the remaining bonds from phosphorus are to one or more of (i) a carbon atom of a $C_1$–$C_{10}$ alkyl group, a benzyl group, a carboxamido $C_1$–$C_6$ alkyl group whose amido nitrogen atom has the formula —$NR^1R^2$ and a phenyl group, and (ii) an O—$R^1$ group, wherein $R^1$ and $R^2$ are the same or different and are a hydrido group, a $C_1$–$C_{10}$ alkyl group, a phenyl group or a benzyl group, (iii) a —$NR^1R^2$ group and (iv) a divalent radical selected from the group consisting of an imino group, a $C_1$–$C_{10}$ cyclic or acyclic hydrocarbylene group, a phenylene group and a xylylene group, where each of the $R^1$ and $R^2$ groups is the same or different and is as defined for $R^1$, and maintaining that contact for a time period sufficient for said bismuth-213 ions to be bound by the first separation medium to form bismuth-213-laden separation medium and a daughter-depleted parent-daughter solution;

(b) removing the daughter-depleted parent daughter solution from the separation medium;

(c) stripping the daughter radionuclide from the daughter-laden separation medium with an aqueous salt solution buffered at a pH value of about 3 to about 7 to form an aqueous solution of bismuth-213 ions; and (d) contacting the aqueous solution of bismuth-213 ions with a second separation medium that is a particulate sulfonic acid polymeric cation-exchange resin having a decontamination factor between parent and bismuth-213 daughter radionuclide under the conditions of contact is about $10^2$ or more, and maintaining that contact for a time period sufficient for said parent radionuclide to be bound by the second separation medium to form a solution of trivalent bismuth-213 daughter radionuclide that is substantially free of divalent radium-225 and trivalent actinium-225 parent radionuclide ion impurities.

24. The method according to claim 23 wherein the hydrochloric acid concentration of the solution of step (a) is about 0.1 M.

25. The method according to claim 23 wherein the stripping solution has a pH value of about 3.5 to about 5.5.

26. The method according to claim 25 wherein the stripping solution contains about 0.75 M NaCl in an about 0.50 M sodium acetate buffer solution at pH=4.0, or 0.75 M $NH_4Cl$ in 0.50 M ammonium acetate buffer solution at pH=4.0.

27. The method according to claim 23 wherein the combined decontamination factor of the bismuth-213 daughter from the parent radionuclide impurities of both the first and second separation media under the conditions of contact is about $10^5$ or greater.

28. The method according to claim 23 including the further step of recovering said solution of trivalent bismuth-213 daughter radionuclide that is substantially free of divalent radium-225 and trivalent actinium-225 parent radionuclide ion impurities.

* * * * *